(12) United States Patent
Williams

(10) Patent No.: US 7,935,130 B2
(45) Date of Patent: May 3, 2011

(54) TWO-PIECE END-EFFECTORS FOR ROBOTIC SURGICAL TOOLS

(75) Inventor: Matthew Reagan Williams, Walnut Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 790 days.

(21) Appl. No.: 11/865,061

(22) Filed: Sep. 30, 2007

(65) Prior Publication Data

US 2008/0119870 A1 May 22, 2008

Related U.S. Application Data

(60) Provisional application No. 60/866,146, filed on Nov. 16, 2006.

(51) Int. Cl.
*A61B 17/00* (2006.01)

(52) U.S. Cl. ............ 606/208; 606/51; 606/52; 606/205; 606/207

(58) Field of Classification Search .............. 606/51–52, 606/205–208
See application file for complete search history.

(56) References Cited

U.S. PATENT DOCUMENTS

| | | | |
|---|---|---|---|
| 920,092 A | 4/1909 | Slaughter | |
| 1,057,423 A | 4/1913 | Haynes | |
| 1,359,164 A | 11/1920 | Lo Giudice et al. | |
| 1,645,981 A | 10/1927 | Benedict | |
| 1,754,806 A | 4/1930 | Stevenson | |
| 2,512,334 A | 6/1950 | Johnson | |
| 2,518,994 A | 8/1950 | Miller | |
| 2,852,846 A | 9/1958 | Ahlbin | |
| 2,939,213 A | 6/1960 | Daniel | |
| 3,688,402 A | 9/1972 | Shannon | |
| 3,750,282 A | 8/1973 | Eaton et al. | |
| 3,816,920 A | 6/1974 | Sastri | |
| 3,894,336 A | 7/1975 | Desimone | |
| 3,895,636 A | 7/1975 | Schmidt | |
| 4,248,231 A | 2/1981 | Herczog et al. | |
| 4,950,273 A | 8/1990 | Briggs | |
| 5,069,872 A | 12/1991 | Penoza | |
| 5,152,778 A | 10/1992 | Bales, Jr. et al. | |
| 5,176,695 A | 1/1993 | Dulebohn | |
| 5,234,453 A | 8/1993 | Smith et al. | |
| 5,330,471 A | 7/1994 | Eggers | |
| 5,366,466 A | 11/1994 | Christian et al. | |
| 5,630,812 A | 5/1997 | Ellman et al. | |
| 5,649,956 A | 7/1997 | Jensen et al. | |
| 5,662,647 A | 9/1997 | Crow et al. | |
| 5,807,378 A | 9/1998 | Jensen et al. | |
| 5,968,074 A * | 10/1999 | Prestel | ......................... 606/205 |

(Continued)

OTHER PUBLICATIONS

Wikipedia, "Austentite," downloaded Sep. 26, 2007 at 12:18 p.m. 2 pages, Internet: http://en.wikipedia.org/wiki/Austenite.

(Continued)

*Primary Examiner* — Linda C Dvorak
*Assistant Examiner* — Jaymi Della

(57) ABSTRACT

In one embodiment of the invention, a robotic surgical tool having opposing jaws, the working element of the robotic surgical tool is made of a different material from the drive element of the robotic surgical tool. The two elements may be manufactured independently and assembled together at a later stage. The material comprising each element may thus have properties more appropriate to the function each element plays in the robotic surgical tool. For example, the metal selected to comprise the blade of a surgical scissor may be corrosion resistant and capable of being sharpened to a high degree.

6 Claims, 15 Drawing Sheets

U.S. PATENT DOCUMENTS

| | | |
|---|---|---|
| 6,090,107 A | 7/2000 | Borgmeier et al. |
| 6,102,909 A | 8/2000 | Chen et al. |
| 6,113,596 A | 9/2000 | Hooven et al. |
| 6,132,441 A | 10/2000 | Grace |
| 6,206,903 B1 | 3/2001 | Ramans |
| 6,309,397 B1 | 10/2001 | Julian et al. |
| 6,331,181 B1 | 12/2001 | Tierney et al. |
| 6,394,998 B1 | 5/2002 | Wallace et al. |
| 6,436,107 B1 | 8/2002 | Wang et al. |
| 6,464,701 B1 | 10/2002 | Hooven et al. |
| 6,491,691 B1 | 12/2002 | Morley et al. |
| 6,994,708 B2 | 2/2006 | Manzo |
| 7,367,973 B2 | 5/2008 | Manzo et al. |
| 2004/0044363 A1* | 3/2004 | Fowler .......................... 606/205 |

OTHER PUBLICATIONS

Vertut, Jean et al., *Robot Technology: Teleoperation and Robotics Evolution and Development*, 1986, vol. 3A, 332 pages, English translation Prentice-Hall, Inc., Inglewood Cliffs, NJ, USA.

\* cited by examiner

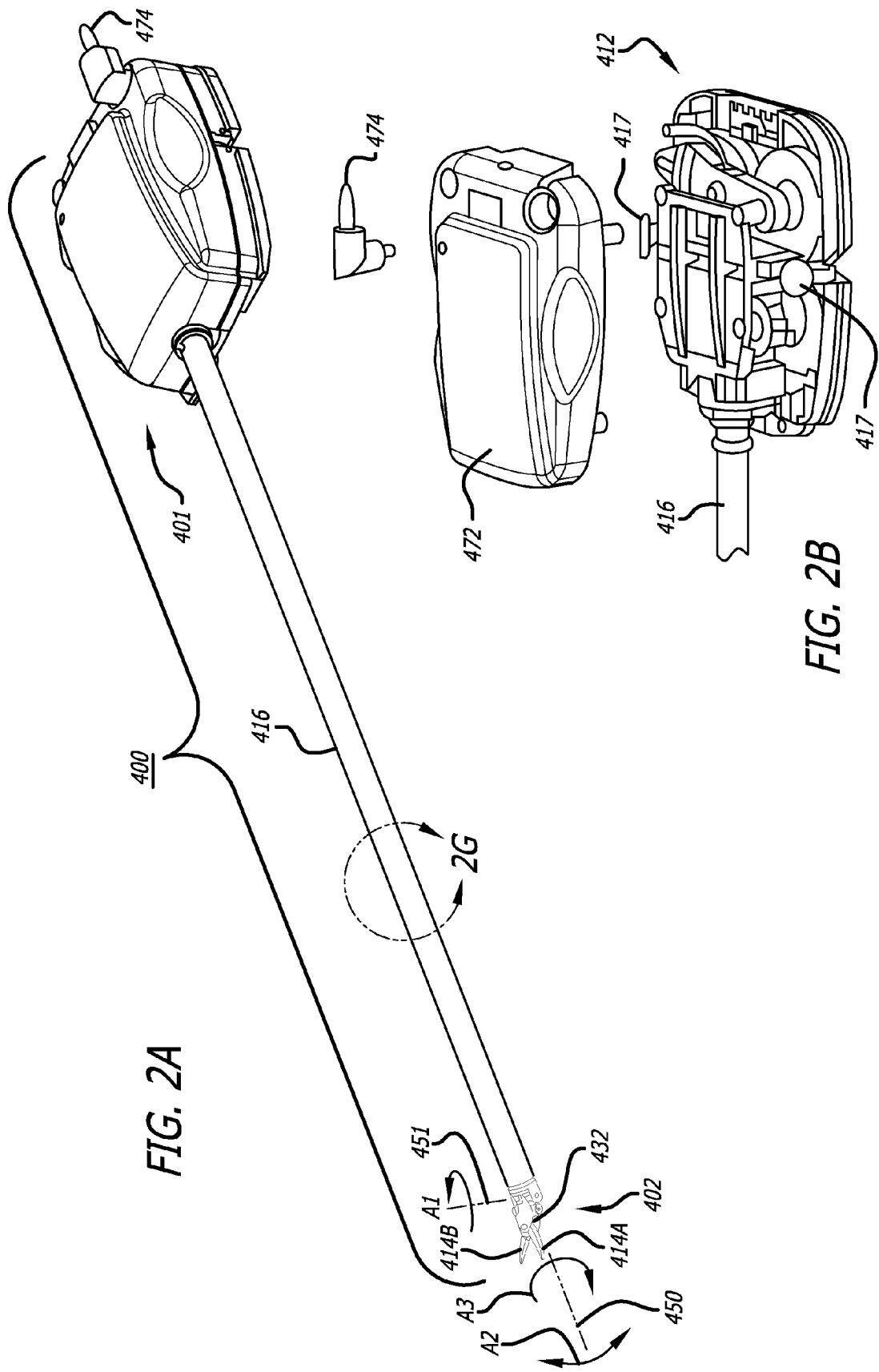

TWO-PIECE END-EFFECTORS FOR ROBOTIC SURGICAL TOOLS

CROSS REFERENCES TO RELATED APPLICATIONS

This non-provisional United States (US) patent application claims the benefit of U.S. provisional patent application No. 60/866,146 entitled TWO-PIECE JAW FOR SURGICAL INSTRUMENTS, filed by Matthew Williams on Nov. 16, 2006, the full disclosure of which is incorporated herein by reference.

FIELD

The embodiments of the invention generally relate to robotic surgical instruments.

BACKGROUND

The manufacture of both curved and straight scissors has been a persistent problem in robotic surgical tools. Two design considerations for the manufacture of robotic surgical scissors are performance and corrosion.

The ability to cut delicate and tough tissue in a human body is limited because the force available to the robotic surgical scissors jaw blades is limited. For most robotically assisted surgery, small scissors are used because the surgical instruments must pass though small ports into a patents body. The robotic surgical scissors are generally connected to a narrow shaft allowing a surgeon to manipulate the scissor inside the patient's body. The size of the scissors, and the length and narrowness of the shaft constrain the amount of power that can be applied to the scissor blades. Limitations on power can be alleviated somewhat by a sharper cutting edge. An exceptionally sharp blade therefore is preferable in robotic surgical scissors. Additionally, robotic surgical scissors are preferably designed to cut in a controlled manner over a range of motion of the jaw blades.

Sharper blades generally lead to better scissors. Sharper blades may be achieved by using a harder metal that can be sharpened to and hold a finer edge. The type of metal alloy selected to manufacture a blade and the sharpening technique (e.g., honing and stropping) employed to sharpen an edge can improve scissor performance.

Sharp robotic surgical scissors typically cut better than dull robotic surgical scissors. Hard metal alloy materials, such as Martensitic stainless steels, may be used to form the jaw blades as it can be ground and honed to a fine edge. In a more general sense, martensite is used to describe crystals which have changed geometries following rapid cooling. The term is applied to describe metals or metal alloys that have been tempered in a heating process and then rapidly cooled, usually by quenching. Martensitic stainless steel is exceptionally hard and can hold a keen edge but at the same time they are extremely brittle. A pair of surgical scissors formed out of Martensitic stainless steel may shatter if dropped on a hard surface.

Honing an edge onto a blade can be an intricate and laborious process. In a honing process, a first side of a blade edge is applied to a grinding wheel or other abrasive device until a burr forms. The presence of the burr means that the steel is thin enough at the top so that it is folding over slightly. Once the burr is formed on a first side, the process is repeated on the second side of the blade edge opposite the first side. Honing a blade in this manner typically results in a very thin and razor sharp edge. The very thin and razor sharp edge is often referred to as a wire edge. The wire edge however is fragile and will likely break off during the very first use, leaving an extremely dull blade. The reason for this structural weakness is that the wire edge is too thin and there is not enough metal left at the edge for strength. After honing, a stropping process may be used to strengthen a wire edge.

Stropping is essentially the removal of the wire edge by brushing the edge of a newly honed blade over a softer surface usually impregnated with some abrasive compound such as stropping paste or green chromium oxide. Jewelers rouge is also acceptable. Leather is a typical strop, often used by barbers, being just firm enough to strengthen a wire edge without dulling it completely.

The honing and stropping process may be complex and labor intensive if performed manually. In sharpening blades on a commercial scale, sophisticated machinery is often used to handle the blades as they are honed. Manufacturing equipment holds the blades in contact with a grinding surface at a predetermined angle with a predetermined pressure. The predetermined angle and pressure may be maintained consistently along the entire blade edge to achieve a uniform sharpness. Generally scissor blades that are flat and uniform in size are easier to sharpen than oddly shaped scissor blades with non uniform proportions.

By their very nature, surgical scissors are prone to stress-corrosion, specifically chemically assisted degradation. A scissor cuts at the intersection of the two blades. In more effective scissors, the blades tightly press against each other. It is difficult for a very sharp scissor blade to cut properly if the fastener (e.g., rivet, bolt, or screw) that couples the blades together is loose. In some scissor designs, the scissor blades slightly curve inward to facilitate contact. The constant contact between scissor blades causes stress fields in the blades themselves, specifically at the edges. A stress field in the blades of the robotic surgical scissors is due to the scissors blades pressing against each other.

Harder metals can hold a sharper edge but tend to be more brittle. Moreover, the harder the cutting blades are made to provide sharp edges in the robotic surgical scissors, the more vulnerable they are to corrosion caused by the presence of a stress field. The hard brittle metal used in most surgical blades is particularly vulnerable to stress related chipping and cracking.

Corrosive materials may be present during surgery. For example, saline is often used during surgery to irrigate tissue in the surgical site. Saline may promote corrosion of the materials used in the manufacture of robotic surgical scissors. Typical rust inhibitors, such as oil based lubricants, are not suitable for use in surgery because of the sterile nature of the surgical site and the risk of contamination and infection. Even though surgical tools are often made of stainless steel because of its corrosion resistant properties, the surgical tools may be experience a corrosive effect on its materials.

Corrosion at the sharpened edge of a blade can result in a duller blade. Additionally, corrosion and the stress field may further weaken the already brittle wire edge causing small flakes of metal to break off inside a patient's body. The corrosive effect on the materials and the stress field may eventually cause a jaw blade to become unusable or fail, such as by cracking (stress fractures) and breaking and falling off from the robotic surgical scissors. A material failure in end effectors of a robotic surgical tool, such as a scissors blade, is undesirable when surgery is being performed within a patient.

One solution to reduce the effects of corrosion and stress fractures in surgical instruments is to replace them often. Newer scissors will be sharper and have less time to corrode. The problem with this simple solution is the cost of replacing robotic surgical tools. Ideally surgical scissors would be replaced after every surgery but doing so is expensive.

Each jaw blade of robotic surgical scissors are typically manufactured using a single material to form both a cutting blade and a drive hub together as one piece. Typically, a cable directly attaches to the drive hub of each jaw blade to lever and pivot the jaw blades around a fulcrum. One example of such a scissors mechanism is used in robotic surgical tools with the DAVINCI™ robotic surgery system made by Intuitive Surgical, Inc. of Sunnyvale, Calif.

As both the drive hub and the cutting blade are typically manufactured together using the same material, they may be manufactured together as one in the same process, such as through a forging process. However by being manufactured together using the same material during the same manufacturing process, a materials compromise may be made between the design requirements for the drive hub and the design requirements for the cutting blade.

The metal alloy used for a typical surgical scissor must be hard and capable of holding a fine edge. Such a metal alloy is also typically brittle. The drive element on the other hand, does not require the same material property.

Moreover manufacturing the drive hub and the cutting blade together as one piece using the same material during the same process forms a complex shape that may increase manufacturing costs. The complex shape also makes it more difficult to sharpen the cutting edge.

BRIEF SUMMARY

The embodiments of the invention are summarized by the claims that follow below.

BRIEF DESCRIPTION OF THE DRAWING

FIGS. 2A-2I illustrate various views of elements of exemplary robotic electrosurgical instruments in which various implementations of the invention may be used.

DETAILED DESCRIPTION

Figure 1A:
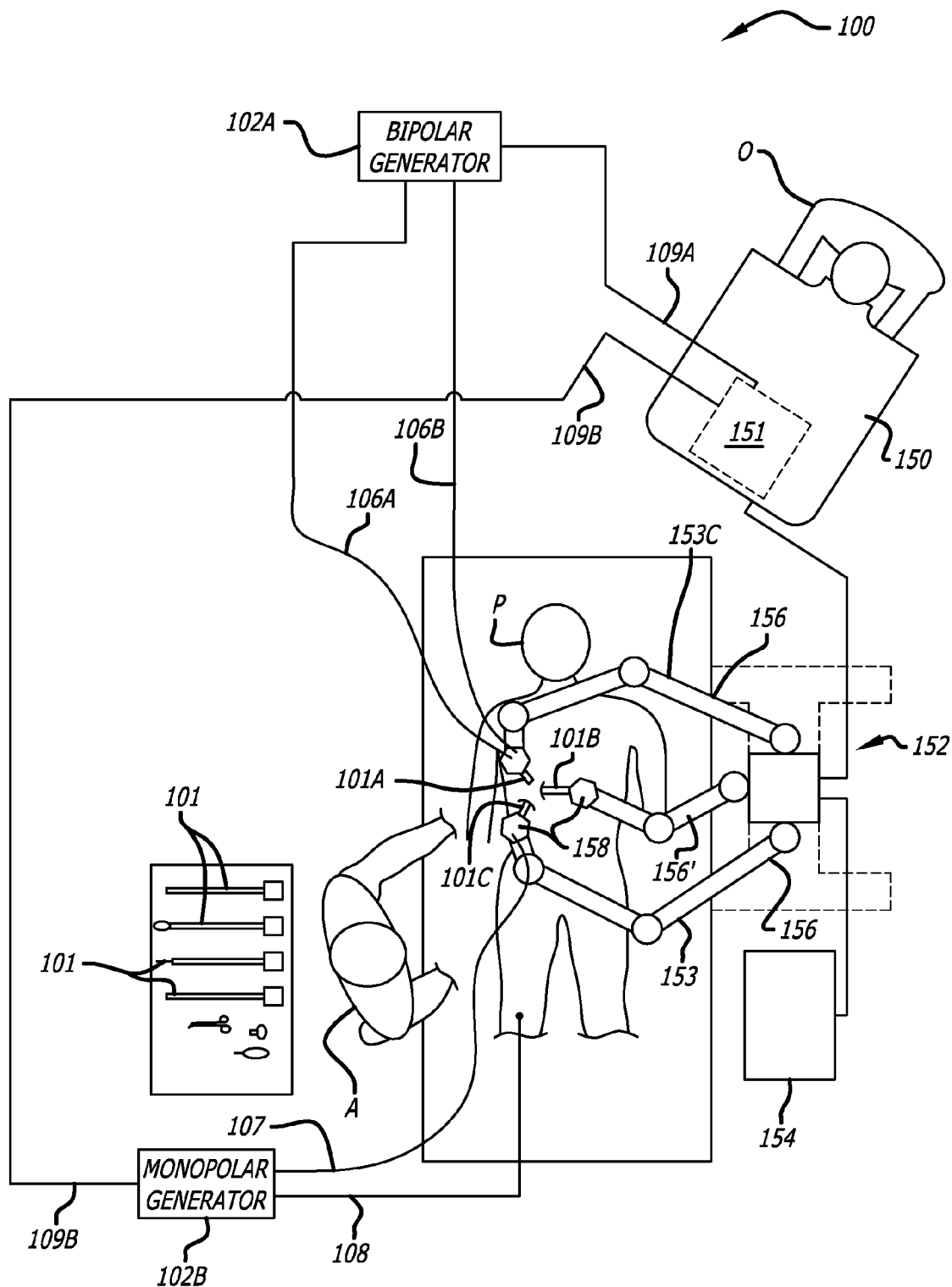
FIGS. 1A-1D illustrate various views of elements of an exemplary robotic electrosurgical system in which various implementations of the invention may be used.

This detailed description describes embodiments that are illustrative of the invention, and so is explanatory and not limiting. The invention is limited only by patented claims. In the drawings, some elements have been omitted so as to more clearly show the embodiments of the invention. Like element numbers in the different drawings are associated with the same or similar elements but may have a different configuration.

INTRODUCTION

The embodiments of the invention include an apparatus and system as well as method of assembly of robotic surgical instruments or tools used in robotic surgical systems. The instruments of the present invention are capable of treating tissue while cutting or shearing treated tissue. The electrosurgical treatment may further reduce bleeding of tissue by cauterizing tissue and coagulating blood. The invention incorporates innovations to reduce the cost of manufacture of end effectors and thereby reduce problems associated with corrosion and dull blades. End effectors may be clamps, graspers, scissors, staplers, needle holders, etc generally actuated by a drive mechanism.

Each end effector is constructed of two pieces, one part to perform the surgical task, and another part to perform the drive task. With separate pieces to the end effector, the design of the features of each piece and its manufacture may be separated, each piece being tailored according to their tasks.

As the tasks of the drive element or drive hub with the drive tasks typically remain constant, it may retain the material properties and features required to interface with the drive system across different tools. The second part, the working element, can take on the properties necessary for the surgical task and differ from tool to tool. That is, the two parts do not have to be made by the same process. Nor do the two parts have to be made of the same material.

Each jaw or pair of end effectors of a robotic surgical instrument or tool is made of two pieces that are mechanically coupled together. The first piece, a working element, performs a surgical task, such as cutting or gripping. The second piece, a drive element, performs the drive task for the first piece. The two pieces are removably coupled by being keyed together thereby avoiding the expense and complications of permanently attaching the two pieces together by using, e.g., brazing, welding, or forging. The second piece, the drive element, receives a force from a force element. The two pieces are keyed together and form pocket for a cable crimp, and a race track to support the cable. The drive force may be transmitted by a cable to the piece with the drive tasks.

In one implementation, the drive element is a drive hub, the force element is a cable attached to the drive hub, and the working element is the cutting blade of a scissors. The cable is activated by a servo motor that is part of a drive mechanism of a robotic surgical system to generate the force to apply of the drive hub and the blade of the scissors.

The ability to process the parts differently is of particular advantage in making robotic surgical scissors. The blades may be manufactured as a flat or nearly flat piece so that they can be sharpened & honed along their entire length. The drive hub needs no sharpening or honing. As a separate piece, the drive hub is detached from the working element to avoid obstructing the scissor blades when sharpened or honed so a higher quality blade may be made.

Referring momentarily to FIG. 1A, a robotic surgical system 100 includes robotic surgical tools 101A-101C (collectively referred to by reference number 101) to perform minimally invasive robotic assisted surgery. The robotic surgical tools 101A-101C may include end effectors 812A-812B such as shown coupled to the robotic surgical tool 400 in FIG. 1D.

The robotic surgical tools 101A-101C may be mounted to and dismounted from a surgical work station or patient side cart 152 that is coupled to a control workstation or surgeon's console 112. The workstation 112 is coupled to cart 152 such that commands from the workstation 112 may be transmitted to the cart 152. While in use, the cart 152 is positioned adjacent to a surgical patient P as illustrated in FIG. 1A.

Figure 1B:
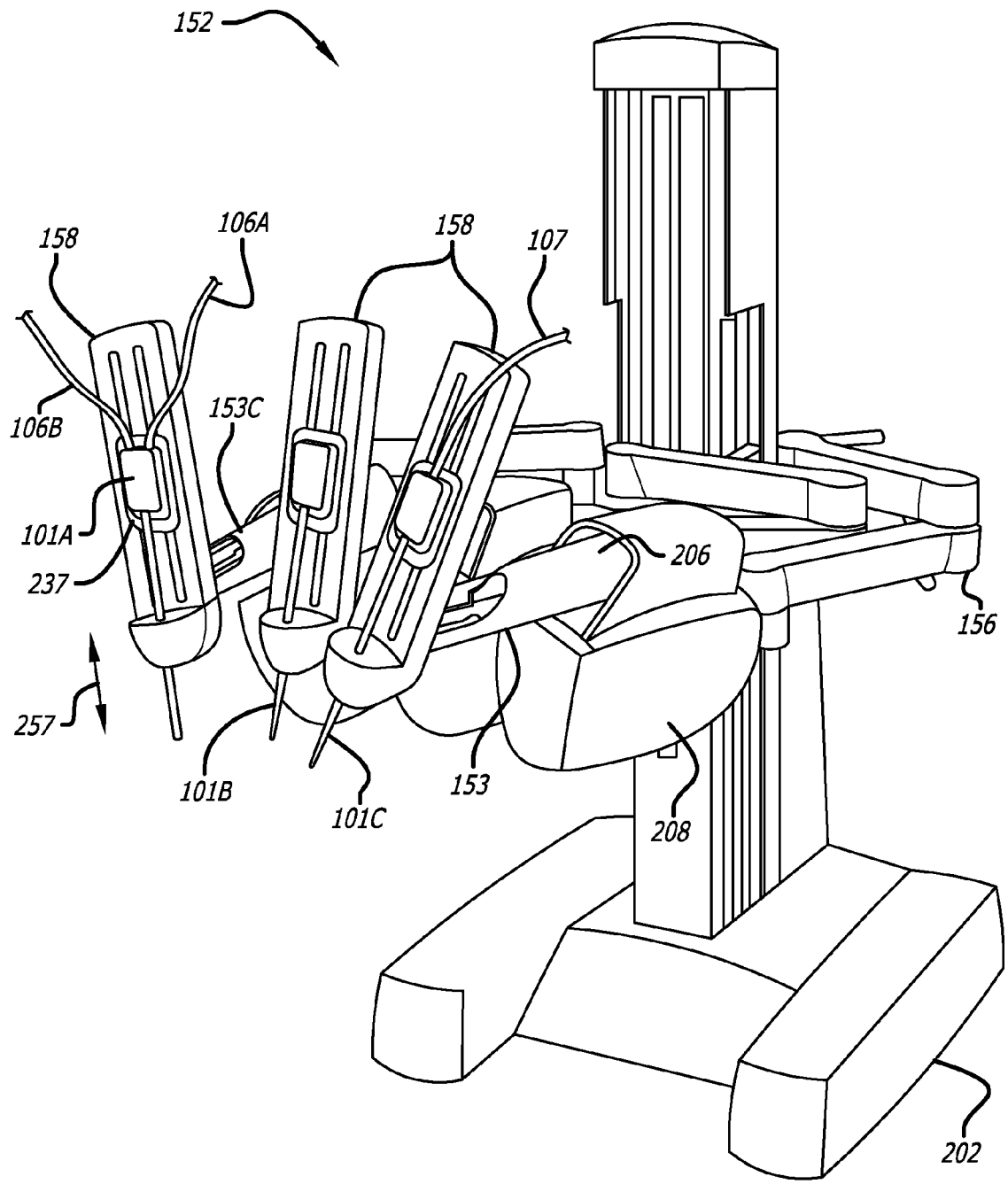

Referring momentarily to FIG. 1B, the cart 152 includes a plurality of robotic arms 153 to which the robotic surgical tools 101A-101C may couple. The robotic arms 153 may be adapted to hold and manipulate interchangeable surgical instruments (such as electrosurgical tools), optical sensors, or patient telemetry sensors as the need arises. The robotic arms may include a sled 158 that includes drive mechanisms to control the position of the robotic surgical tools and the associated end effectors, if any.

Figure 1C:
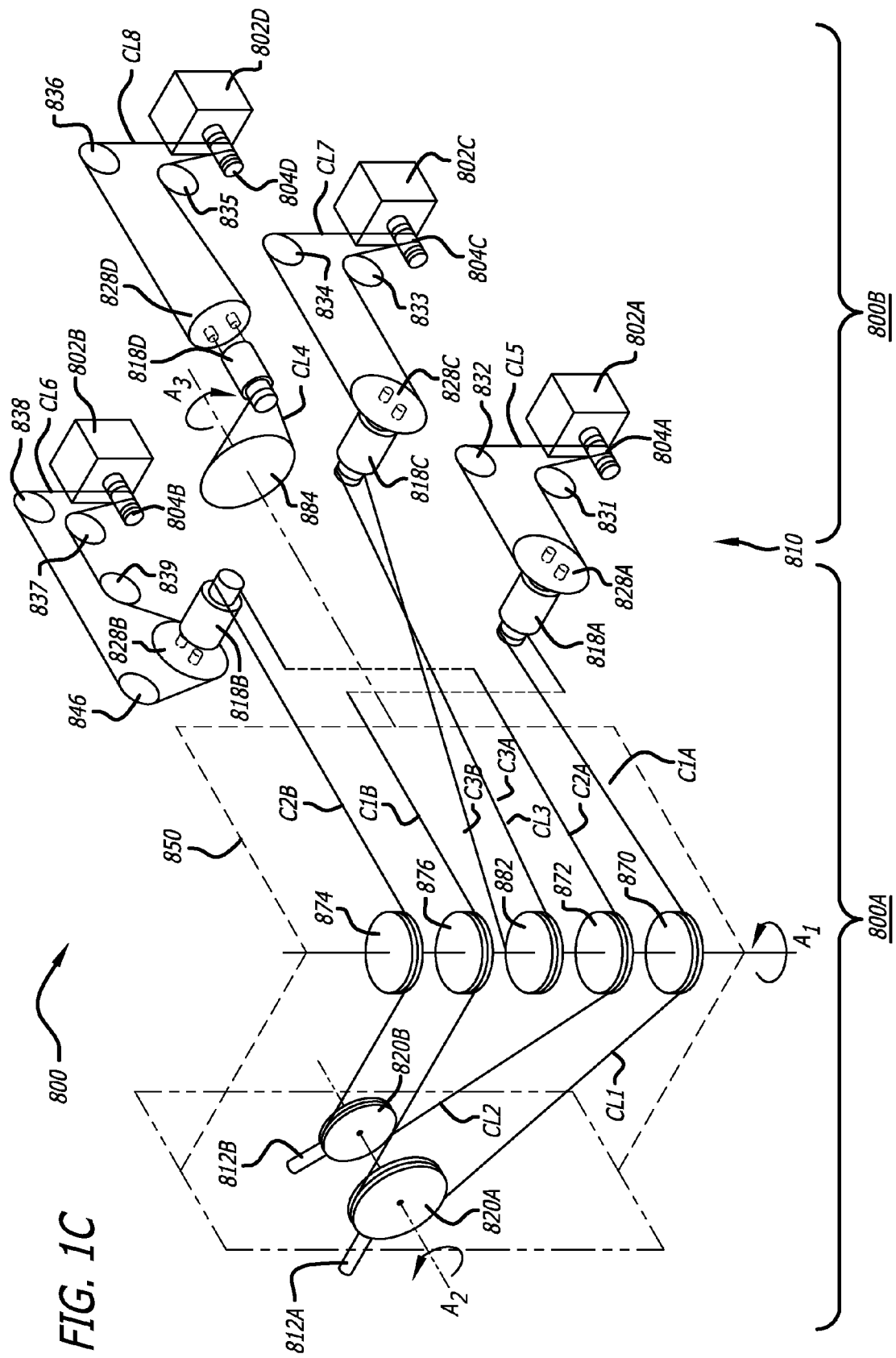
Figure 1D:
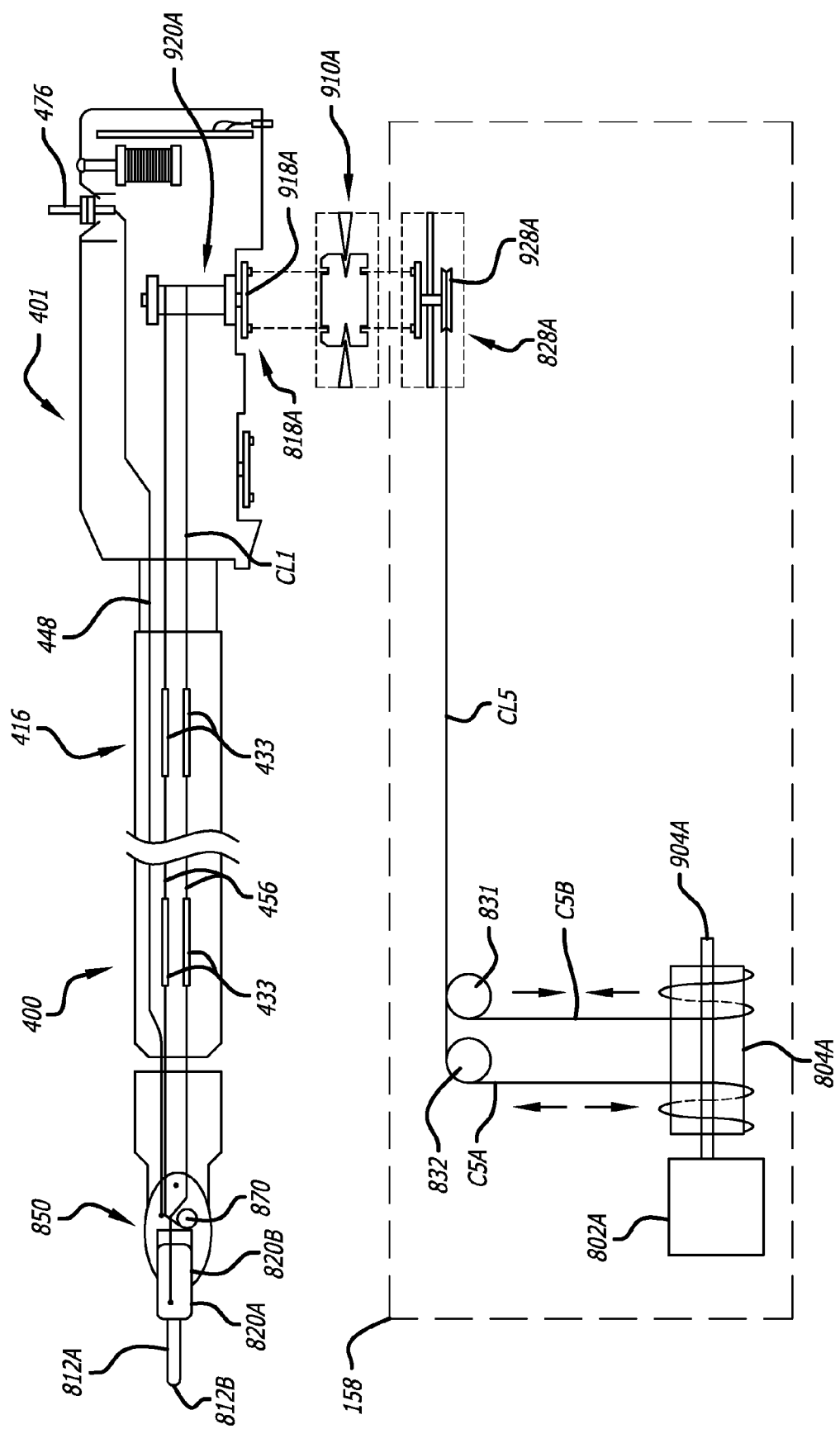

Referring momentarily to FIGS. 1C-1D, schematic views of the drive mechanisms in the sled 158 and the robotic instrument 400 are illustrated. The end effectors 812A-812B may be two-piece end effectors at the distal end of the robotic instrument. The drive mechanisms provide tension in cable loops that is applied to drive elements of the end effectors which is then translated to the working elements. The robotic instrument 400 may be an electro-surgical robotic instrument with two-piece end effectors adapted to receive electrical energy and couple it to tissue. The end effectors 812A-812B may have a plurality of movement provided by a pivotal wrist 850, such as a multi-pivot wrist, a distal roll joint, or other joint or wrist like mechanism.

Referring momentarily to FIGS. 2A-2I, further details of the structure of the exemplary robotic instrument 400 are illustrated. End effectors 414A-414B may be two-piece end effectors at the distal end of the robotic instrument 400. The end effectors 414A-414B may have a plurality of movement provided by a pivotal wrist 402. In one implementation, the robotic instrument 400 may be an electro-surgical robotic instrument.

Two-Piece Robotic Surgical End Effectors

Figure 3:
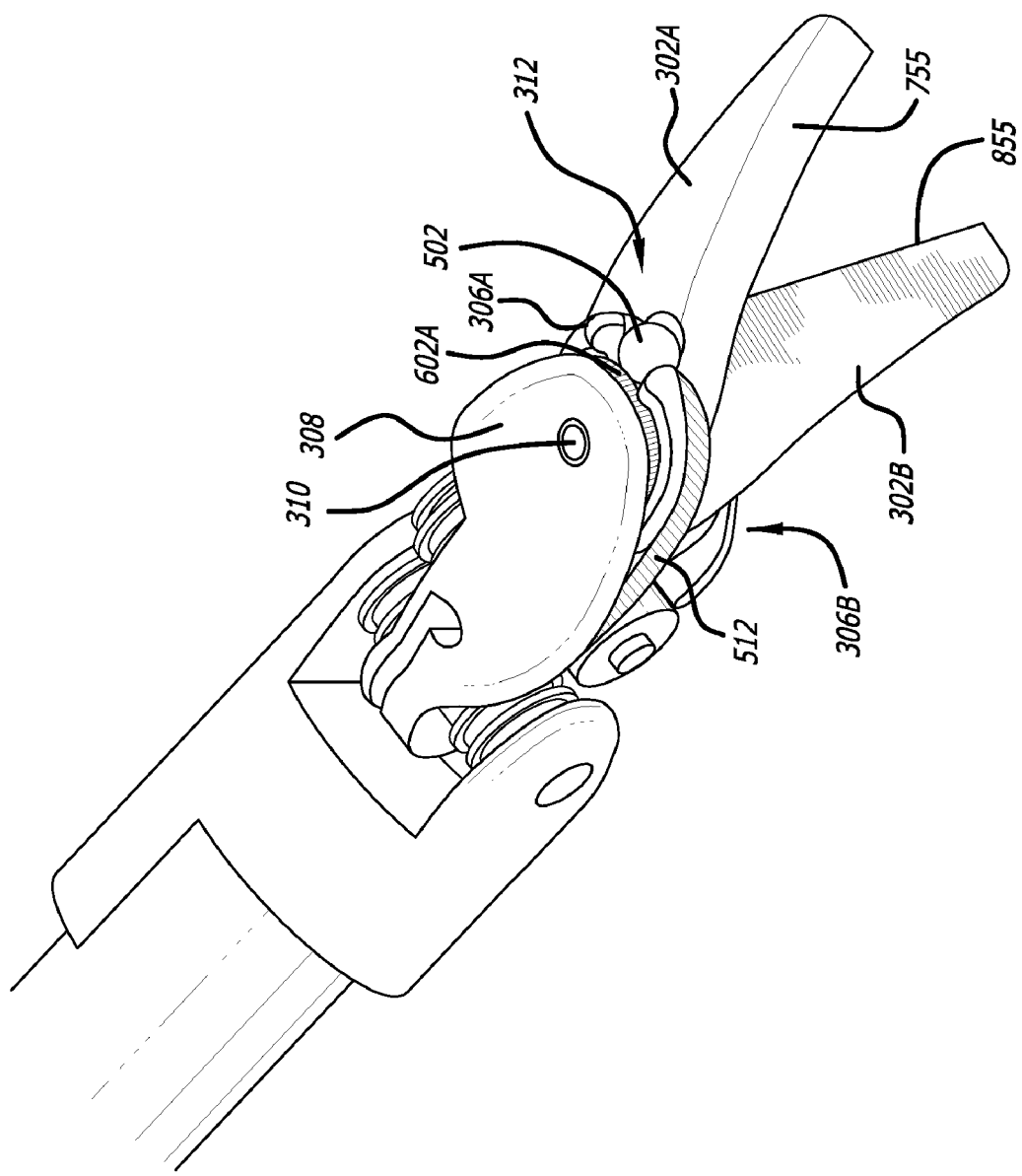
FIG. 3 is a perspective view of robotic surgical scissor end effectors.

FIG. 3 is a perspective view of robotic surgical end effectors at a distal end of a robotic surgical instrument or tool. As shown in FIG. 3, the end effectors are two jaws pivotally coupled together. In this illustrative embodiment of the invention, the jaws or end effectors act as surgical scissors. While curved scissors are shown and described herein, straight scissors may be similarly configured with each end effector being formed of two pieces keyed together. In some embodiments of the invention, the jaws or end effectors may act as grippers, such as forceps or needle drivers. In some embodiments both jaws or end effectors are movable. In other embodiments, one jaw or end effector is fixed while the other jaw is movable.

Each jaw or end effector shown in FIG. 3 is made of two pieces. The first piece 302A, 302B is the working element, such as a scissors blade. The second piece 306A, 306B is a drive hub that acts as a lever to move the first piece 302A, 302B. As shown in FIG. 3, the drive hub receives force from a cable (512). The first piece 302A, 302B and second piece 306A, 306B are removably keyed together so that they move together as a single piece. The two jaws or end effectors are held in a clevis 308 and pivot around a clevis pin 310. As shown in FIG. 3, in one embodiment a cable crimp pocket 312 and a cable track is formed by and in between the first piece 302A, 302B and the second piece 306A, 306B.

The two-piece configuration of each jaw or end effect allows each piece to be optimized for its task, both for manufacturing and for use. In one implementation, the working element or first piece 302A, 302B is a scissors blade that is stamped from a hard metal alloy such as Austenitic stainless steel. Austenitic stainless steel (or gamma phase iron) is a metallic non-magnetic solid solution of iron and an alloying element. The alloying elements, such as manganese and nickel, can stabilize the austenitic structure, facilitating heat-treatment of low-alloy steels. In austenitic stainless steel, much higher alloy content makes the austenitic structure stable at room temperature.

To avoid stress corrosion, the edge of the blade, but not the body, is cold worked during manufacturing and then sharpened. The drive element or second piece 306A, 306B is made from a softer metal alloy or steel that is more appropriate for cable actuation. The two pieces simplify manufacturing of the surgical tool as they can be made separately out of different materials and through different manufacturing process and they are shaped so that it is simple to fit each piece together. Moreover, it may be less costly to make the two separate pieces than it is of combining them together into a single piece, including the working and drive elements, or permanently attaching the working and drive elements together, such as through welding or brazing.

Scissors blades may be manufactured as a flat or nearly flat piece so that they can be sharpened and honed along their entire length. If the drive hub and scissor blade are manufactured together out of a one piece design, the drive hub may interfere with the sharpening/honing and stropping of a scissors blade. The two-piece design may allow a higher quality cutting blade to be manufactured at a reduced overall manufacturing cost. Moreover, during refurbishment of a robotic surgical tool and its end effectors, replacement of a scissors blade separate from the drive hub may be less costly than replacing a one piece combined drive hub and blade.

The two-piece design of the end effectors provides the ability to tune the material, manufacturing and post-manufacturing processing of the working element and the drive element. The material, manufacturing and post-manufacturing process of the working element may be chosen independently of the drive element so that the working element has properties better suited to the surgical task. The material, manufacturing and post-manufacturing processing of the drive element may be chosen independently of the working element so that the drive element has properties better suited to its driving tasks. The two-piece design of the end effectors allows flexibility in choosing the blade material and the hub material, their manufacture and post-manufacture processing, which results in a sharper blade with better cutting performance at a lower cost.

With two-piece end effectors, the blade material and the hub material can differ. For example, the material out of which the working elements 302A and 302B may be formed is a metal alloy, such as Austenitic stainless steel, that is more corrosion resistant. The drive element can be made of a different metal alloy, such as Martensitic stainless steel, that is a more durable alloy and better suited to its task of anchoring a cable, receiving a torque from the cable and transferring the torque to the working element.

With two-piece end effectors, the manufacturing process of the blade and the hub can differ. The working elements 302A and 302B, such as scissors blades may be initially formed or manufactured by stamping or die cutting a metal alloy, such as Austenitic stainless steel for example. The drive elements 306A, 306B may instead be initially formed by stamping, or manufactured by an injection molding process (e.g., injecting a mix of metal and plastic into a mold, and then sintering it in an oven to drive off the plastic).

With two-piece end effectors, the post-manufacturing processes of the blade and the hub can differ. After being manufactured, the drive elements 306A, 306B may undergo hardening by precipitation, for example. Alternatively, the drive hubs might be hardened by heat treating. Without the drive hub being integral with the blade, the two piece design of the end effector allows access to the blade edge which can be processed different from the body of the blade. The blade edge or cutting edge of the scissor blade may undergo local mechanical hardening (e.g., work hardening, cold working by coining, hammering, or forging) prior to grinding so that the cutting edge can be of a different hardness or density from the body of the blade. The local mechanical hardening does not change the overall shape of the part but work hardens the cutting edge of the blade. After the local mechanical hardening of the cutting edge of the blade, the cutting edge may be sharpened by a grinding process and then honed by a stropping and/or polishing process. The post-manufacturing process of a scissors blade can be more extensive than that of the drive hub.

The overall process of formation of the working element provides a blade that is both ductile (e.g. tough) where needed in the body of the blade, yet hard and sharp where needed at the cutting edge. The two-piece end effector design provides freedom to process the blade differently than the hub. The use of austenitic steel for the blade avoids stress corrosion cracking. These features are useful in manufacturing robotic surgical scissors at low cost and when robotic surgical scissors may be re-used over multiple surgeries.

The flexibility in the two-piece design of the end effectors may also be applied to other robotic surgical tools, particularly those tools that have a conflict between the material properties of a drive element and a surgical or working element. That is, the two-piece end effector or jaw design can be applied to other robotic surgery tools other than scissors. For example working elements 302A and 302B may be the jaws of a tissue grasper or a needle driver, instead of the blades of a shear or scissors.

Needle drivers, for example, typically have to be very hard at the point at which they grip the needle. Typically a harder piece of tungsten carbide is brazed onto the working element of the gripping jaw. Instead, the embodiments of the invention allow the entire working grip element to be made of the hard material (e.g., carbide steel) required to grip the needle, while the separate drive element (drive hub) is made of a different material, such as stainless steel. A tungsten carbide grip, the working element, is keyed to the stainless steel drive hub during assembly of the end effectors to the robotic surgical tool. It may be easier to manufacture the complete working grip element out of the hard material and avoid a brazing step. Without a brazing or welding process and the human labor involved to perform the brazing or welding, it may also be less expensive to form two-piece end effectors. Thus, the two-piece design of end effectors may provide complex surgical tools at lower cost with improved quality.

While two end effectors are shown in the drawings, it is understood that in other embodiments of the invention, a single two-piece pivotal end effector may be coupled to the end of the robotic tool shaft. A second end effector may be rigidly coupled in fixed position to the robotic surgical tool. In which case, one drive element 306A may be utilized instead of two. For example one scissor blade without a drive element may remain stationary while the other blade with a drive element moves against the stationary blade forming a single action scissor.

Figure 4A:
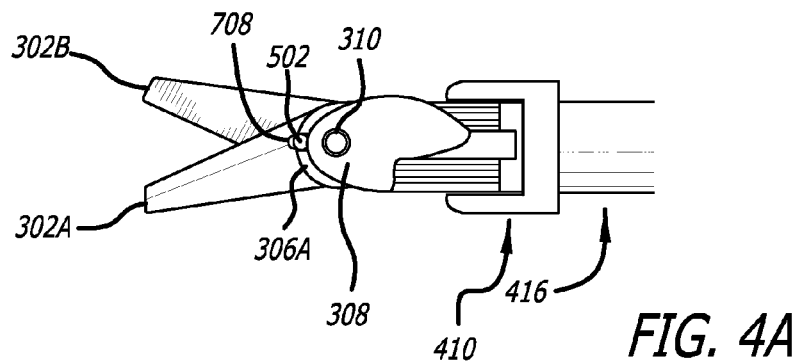
FIG. 4A is a top view of robotic surgical scissor end effectors.
Figure 4B:
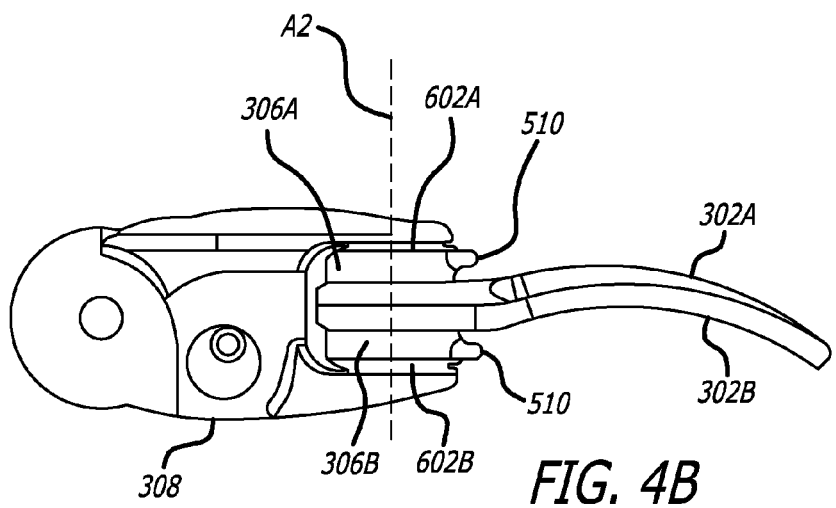
FIG. 4B is a side view of robotic surgical scissor end effectors.

Referring now to FIGS. 4A-4B, a top view and a side view of an exemplary scissors embodiment is illustrated. As shown in FIG. 4A, the jaws are end effectors with at least two degrees of freedom (wristed) positioned at the distal end of the shaft 416 of a minimally invasive robotic surgery tool. One degree of freedom for each end effector is provided by the drive cables 512 (see cable 512 for one end effector in FIG. 5). Other robotic surgical tools using one or more jaws or end effectors may have a similar configuration.

The clevis 308, a pivotal housing with an opening to hold the end effectors, is coupled to the distal end of the shaft 416. If the robotic surgical tool is wristed as shown in FIG. 4A, the clevis 308 may be pivotally coupled to the distal end of the shaft by a pivot pin 410. A cable (not shown in FIGS. 4A-4B) may couple to the clevis to pivot it about the pivot pin near the end of the shaft 416.

A clevis pin 310 with ends coupled to the clevis 308, holds one or more end effectors pivotally coupled to the distal end of the shaft 416. The clevis pin 308, a pivot pin, inserted through pivot holes serves as a pivot point or pivotal axis A2 for the end effectors, including pivot holes in the working elements or blades 302A-302B and the drive elements or drive hubs 306A-306B.

Washers 602A-602B sandwich the drive hubs 306A-306B and the blades 302A-302B together between an opening in the clevis 308 as shown. The washers 602A-602B position the working elements close together. With blades 302A-302B of a scissors, the washers 602A-602B keep the blades tightly fitted against each other to enable them to effectively cut over their range of motion. The washers 602A-602B include a pivot hole to be pivotally coupled to the clevis 308 by the clevis pin 310.

Figure 5:
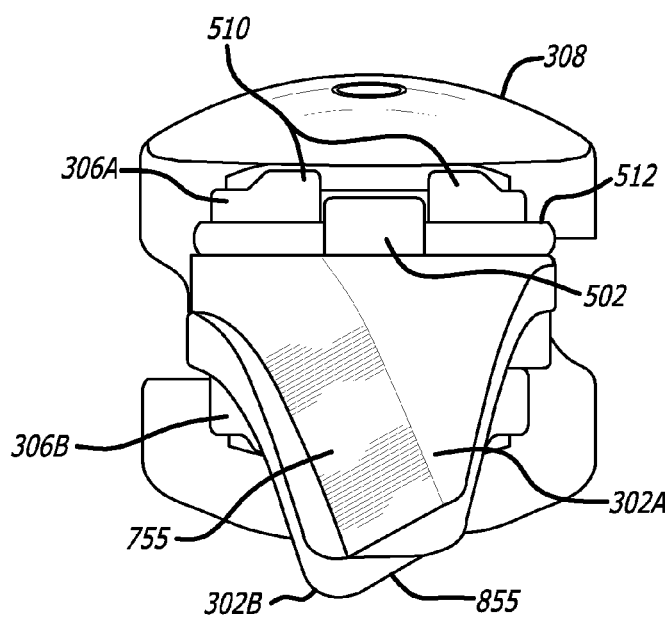
FIG. 5 is a magnified frontal view of robotic surgical scissor end effectors.

FIG. 5 is a magnified front view of the exemplary scissors embodiment of the invention. The clevis 308 houses the drive elements 306A-306B and the blades 302A-302B. The drive elements 306A-306B may each include a pair of prongs or split finger-like protrusions 510 to form a receptacle to receive a crimp 502 of a cable 512. The crimp 502 may rest between the prongs 510 of the drive element (drive hubs 306A-306B) and an opening in the working element (blades 302A-302B). The crimp 502, a metal cylindrical-like shot, may be mechanically coupled to the drive cable 512 by swaging, a metal-forming technique in which the metal is plastically deformed to its final shape using high pressures. The crimp 502 may be formed out of Austenitic Stainless steel to resist corrosion. The drive cable 512 loops around the drive hubs 306A-306B resting in a cable track 706, 806 within a groove (see cable groove 915 in FIG. 9C) around the drive hub. The drive cable 512 is routed back along the shaft towards an actuating spool, such as spool 920A illustrated in FIG. 1D. The cable 512 provides the force that is coupled to the drive element 306A and translated to pivot the blade 302A to provide movement thereof. Another crimp and drive cable may similarly be coupled to the drive element 306B to pivot the blade 302B.

The assembly of the end effectors retains the crimp within a pocket, formed by the prongs and an opening, so that there is no welding or deformation of metal to couple the cable to the drive element so as to avoid corrosion that might otherwise occur. That is after cable assembly, the prongs 510 of the drive element 306 along with the tension in the cable 512 hold the crimp 502 in place without the need to deform the crimp or the prongs.

Figure 6:
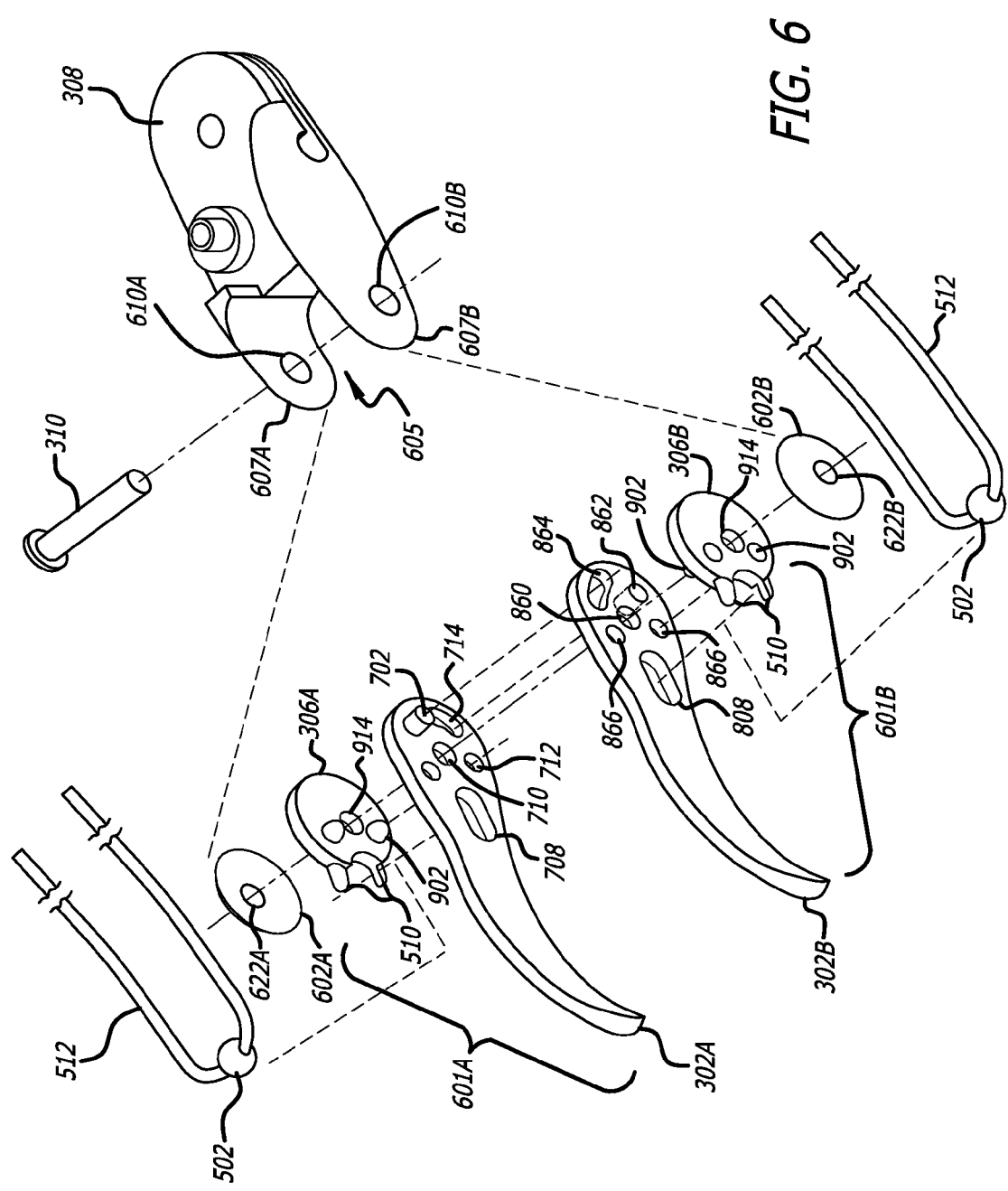
FIG. 6 is an exploded view of robotic surgical scissor end effectors.

Referring now to FIG. 6, an exploded perspective view of a distal end of a robotic surgical tool is illustrated including two-piece end effectors 601A-601B. The clevis 308 includes an opening 605 between a pair of tabs 607A-607B. Each of the tabs 607A-607B includes a pivot pin opening 610A-610B respectively to receive the clevis or pivot pin 310. The width of the opening 605 in the clevis 308 between the tabs 607A-607B is substantially equivalent to the thickness of the elements being pivotally coupled to the clevis, such as the thickness of the washers 602A-602B, the drive elements 306A-306B, and the working elements 302A-302B.

As illustrated in FIG. 6, each of the blades 302A-302B includes an opening 708, 808 in line with the prongs or fingers 510 of the drive elements 306A-306B such that when assembled together a pocket or receptacle is formed to hold the crimp 502 of the cable 512 against the drive element as well as the working elements or blades 302A-302B.

The robotic surgical instrument jaw is assembled by positioning the washers 602A-602B in the opening 605 of the clevis 308. The working elements or blades 302A-302B are respectively keyed to the drive elements or drive hubs 306A-306B to form the end effectors 601A-601B. The working elements or blades 302A-302B are respectively keyed to the drive elements or drive hubs 306A-306B by the one or more drive dogs 902 being coupled into one or more respective drive holes 712, 866. The drive dogs 902 may be press fitted or slip fitted into the one or more respective drive holes 712, 866 so that there is substantially no rotational error between the drive hubs and the working elements. The end effectors 601A-601B are then positioned in the opening 605 of the clevis between the washers 602A-602B.

The pivot pin 310 is inserted into the first pin hole 610A in the tab 607A of the clevis 308; through the respective pivot holes 622A, 914, 710, 860, 914, 622B of the washer 602A, the drive element 306A, the working elements 302A-302B, the drive element 306B, and the washer 602B; and into a second pin hole 610B in the tab 607B of the clevis. The pivot pin 310 pivotally couples the washers, the drive elements, and the working elements together along a pivotal axis concentric with the pivot pin.

A pair of drive cables 512 with a pair of crimps 502 may be assembled (cabled) to the end effectors 601A-601B at different steps in the assembly process of the end effectors to the robotic surgical tool. The drive cables 512 are typically formed of a very hard metal, such as tungsten carbide, to withstand the high tension forces to apply torque to the end effectors. The drive cables 512 may be assembled to the robotic surgical tool after the pivot pin 310 is completely fastened to the clevis 308 or during assembly of the end effectors. If a cable 512 fails for some reason, it may be replaced in the scissors without removing the clevis pin 310. The old cable may be slid out and a new cable slid back into the end effector assembly. If a cable 512 fails final test prior to distribution, it may also be replaced with a new cable to meet the final testing. Thus, the two-piece end effector design may reduce the parts that are scrapped during manufacturing.

In either case, the ends of the cable loop 512 are inserted end first down the shaft of the tool towards the drive spools. The crimp 502 and cable 512 are positioned with respect to the drive elements so that the crimps 512 are positioned between the prongs 510 of the drive elements within the receptacle 708, 808 of the respective blade 302A-302B. From the crimp 512, each cable wraps around the cable groove or channel side 915 of their respective drive hub 306A-306B in their respective race track or cable channel 706, 806 between the drive hub 306A-306B and the blade 302A-302B.

The cables 512 are then tensioned properly at the drive spool. The tension 512 in the cables assist in keeping the crimps 502 in their respective pockets between the prongs 510 and the receptacle 708, 808 in each respective blade 302A-302B. Thus, the cables 512 and the crimps 502 may be assembled to the end effectors 601A-601B without swaging the working elements (e.g., blades 302A-302B) or the drive elements (e.g., the drive hubs 306A-306B) to help avoid stress corrosion in either piece, particularly the scissor blades 302A-302B.

Ends of the pivot pin 310 within the holes 610A-610B may be fastened to the clevis 308 in a number of ways such as by swaging, a friction fit, a screw threading, or a riveting. Alternatively, one end of the pin 310 may include a head to act as a stop while the opposite end of the shaft of the pin is coupled to the clevis.

As mentioned previously, the working elements or blades 302A-302B are respectively keyed to the drive elements or drive hubs 306A-306B. To do so, each of the drive elements 306A-306B include one or more drive protrusions or drive dogs 902 extending from the body of the drive elements. The protrusions 902 are fitted into corresponding openings 712, 866 in an interface portion of the working elements 302A-302B when the end effectors are assembled into the clevis 308 so that the drive elements 306A-306B are keyed to the respective working elements 302A-302B.

At the distal end, the drive cables 512 wrap around the drive elements 306A-306B and are routed through the clevis 308 into the shaft of the robotic surgical tool. The ends of the cable loops may be wrapped around a drive spool at a proximal end of the robotic surgical tool. A tension force in the drive cables is coupled into the drive elements 306A-306B and the working elements or blades 302A-302B as a torque around the pivot pin 310.

With the washers 602A-602B respectively fitted between tabs 607A-607B of the clevis 308 and the drive elements 306A-306B, the working elements 302A-302B may be squeezed together. The washers 602A-602B may be spring loaded, concave, or convex to maintain a force squeezing the working elements together when assembled into the clevis.

Figure 7A:
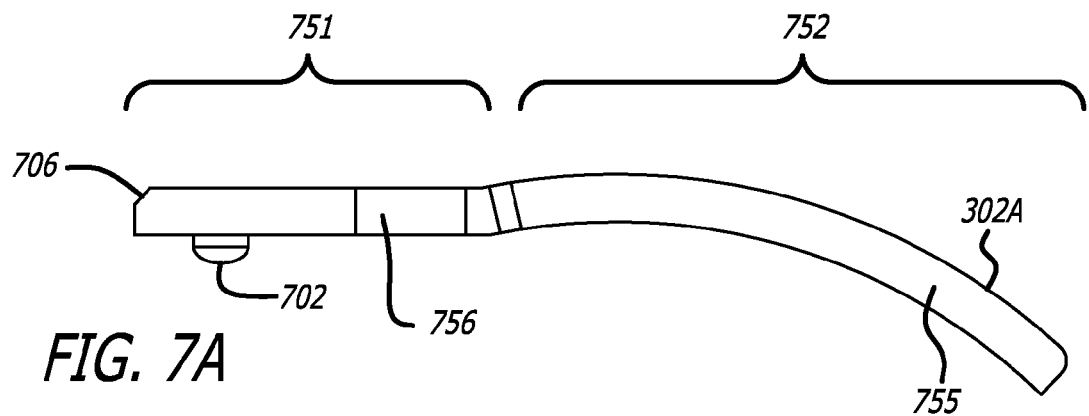
FIG. 7A is a perspective view of the outer blade of the robotic surgical scissor end effectors.
Figure 7B:
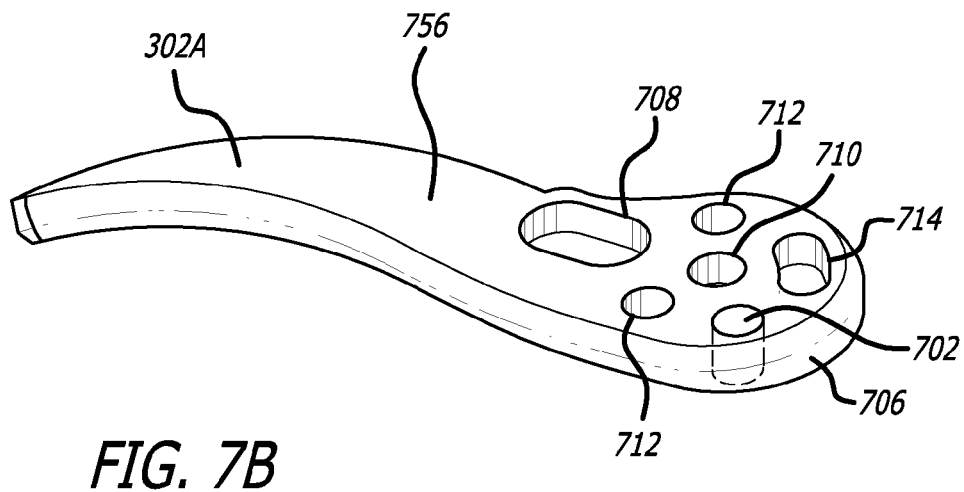
FIG. 7B is a side view of the outer blade of the robotic surgical scissor end effectors.

Referring now to FIGS. 7A-7B, views of a first working element, the outer blade 302A, are illustrated. The outer scissor blade 302A has a drive interface portion 751 and a cutting portion 752 extending there-from. An oval opening 708, also referred to as a crimp receptacle, extends between the drive interface portion 751 and the cutting portion 752. The crimp receptacle 708 may receive a portion of the crimp 502 of a drive cable 512.

The cutting portion 752 of the blade 302A has a sharpened/honed cutting edge 755 to interface with a sharpened cutting edge 855 of the blade 302B. While the cutting edges 755, 855 of the blades may undergo a post-manufacturing process to harden and sharpen them, other parts of the blade, referred to as the body 756, may not undergo those post-manufacturing processes.

The drive interface portion 751 of the blade 302A has a pivot hole or opening 710 and one or more spaced apart drive holes 712, a cam channel 714, and a stop protrusion 702 spaced apart from the pivot hole 710. An edge of the drive interface portion 751 may be chamfered and larger in diameter than the drive hubs 306A-306B. When assembled, the chamfered edge forms a cable channel 706 along which the drive cable may be deployed. The drive channel 706 may help to keep the drive cables 512 aligned and prevent them from catching on external objects.

The pivot hole 710 in the drive interface portion of the blade allows the clevis pin 310 to be inserted through the blade 302A thereby providing a pivot point or pivotal axis around which the outer blade 302A may pivot or rotate.

The drive holes 712 in the drive interface portion 751 of the blade 302A receive drive protrusions 902 (see FIG. 9B) of the drive element or drive hub 306A. This allows the blade 302A to be keyed to the drive element 306A so that a force may be translated from the drive element to the working element.

Keying the drive element 306A to the working element 302A of the end effector does not require a special tool. The simple keying of the drive and the working element together to form an end effector may lead to cost savings.

The cam channels 714, 864 in conjunction with the respective stop protrusions 862, 702 provide mechanical stops to the limit the respective pivotal movement between the blades 302A-302B. The stop protrusion 702 extends out from the drive interface portion 751 of the blade 302A to interface with a cam channel 864 (See FIG. 8B) in the working element 302B when the end effectors are assembled together in the clevis 308 of the robotic surgical instrument. The exemplary embodiment of the cam channels 714, 864 have a kidney-bean-like shape.

At the ends of the cam channel 864 are stops against which the stop protrusion 702 may strike to limit the range of pivotal motion of and the angle between end effectors. The cam channel 714 in the drive interface portion of the blade 302A is similarly shaped with stops at its ends. A stop protrusion 862 (see FIG. 8A) of the blade 302B is received by the cam channel 714 in the blade 302A when the end effectors are assembled together. The stops at the end of the cam channel 714 limit the motion of the stop protrusion 862 and the blade 302B so that the range of motion and the angle between end effectors is limited.

When assembled adjacent to each other and with the stop protrusions 702, 862 inserted into their respective cam channels 864, 714, (see FIGS. 7B and 8B) the range of angles between the blades 302A-302B is limited so as to prevent them from opening too wide and closing too far. That is the cam channels 864, 714 allow a range of movement in the blades. However, when the stop protrusions 702, 862 contact the ends (mechanical stops) of the cam channels, the movement of the blades 302A-302B is mechanically stopped.

In one implementation, the stop protrusions 702, 862 in the respective cam channels 864, 714 limit the angle between the working elements to be no greater than 30 degrees. Opening the blades to an angle greater than 30 degrees may expose large sections of the cutting edges, which may be undesirable in the limited space of a body cavity. If no open stop is provided to scissors, the cutting edges of the blades may become overexposed, and if the robotic surgical tool is inadvertently moved, the overexposed cutting edges may accidentally cut tissue within a surgical site. Thus, either a mechanical stop or a computer controlled stop may be provided to robotic surgical scissors.

At an opposite end, the stop protrusions 702, 862 in the respective cam channels 864, 714 may limit the angle between working elements to be not less than zero degrees or a few degrees of crossover to assure the blades will cut tissue but avoid damage to the blades and the end effector assembly within the clevis and avoid exposing the cutting edge of one blade beyond the trailing edge of the other. The exposure of the cutting edge of the blade when closed is responsive to the thickness of the blade. Adjustments to manufacturing and processing of the scissors blades may be made to adjust the exposure of the cutting edge of the blades when closed.

If no close stop is provided to scissors, the blades 302A-302B may close too far crossing over each other until the cutting edge of one blade has traveled beyond the trailing edge of the other blade and over expose a cutting edge. Robotic surgical tools are often moved in the closed position. If no close stop is provided and the blades are closed to far to over expose a cutting edge, there is greater risk of inadvertent tissue damage within the surgical site.

Referring now to FIGS. 5, 6, 7B and 8B, the crimp receptacle 708, 808 forms part of a crimp pocket which retains the crimp 502 to hold the drive cable 512 coupled to the end effector. In one implementation, the crimp receptacle 708, 808 is an oval hole between the drive interface portion and the cutting portion of the working element. The opening of crimp receptacle 708, 808 is slightly wider than the length of the crimp 502 to properly receive it. The opening of the crimp receptacle 708, 808 is somewhat elongated to allow the crimp to be installed after the end-effector is assembled into the clevis.

During assembly of the cables 512 in the robotic surgical tool, the crimp 502 is slid towards the drive element to be positioned between the two prongs 510 of the drive element within the crimp receptacle 708, 808. The prongs 510 press against the cable 512 on each side of the crimp 502 to keep the crimp 502 within the receptacle 708, 808. The crimp 502 is trapped in a crimp pocket between the prongs 510 of the drive element and the sides of the receptacle 708, 808 in the working element. The crimp is effectively trapped in the crimp pocket without having to deform any metal during assembly so that corrosion may be avoided.

The crimp 502 may be permanently attached to the drive cable 512 prior to the cables 512 being assembled into the robotic surgical tool. In this manner, deformation of the working element (e.g., scissors blades) during the assembly of the end effectors, such as during a crimping process, does not occur so that corrosion may be avoided.

The metal crimp 502 may be attached to the cable 512 in such a way as to leave the crimp intact. One method of achieving this end is to crimp the metal to the cable and then polish the metal crimp. The polishing smoothes out blemishes which may become pockets of corrosion. Alternatively, the metal crimp 502 may be molded around the cable 512 and then polished.

Figure 8A:
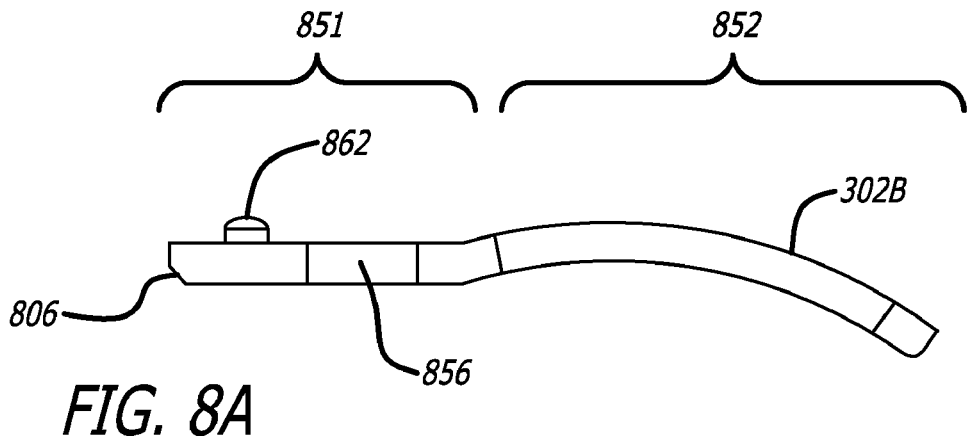
FIG. 8A is a perspective view of the inner blade of the robotic surgical scissor end effectors.
Figure 8B:
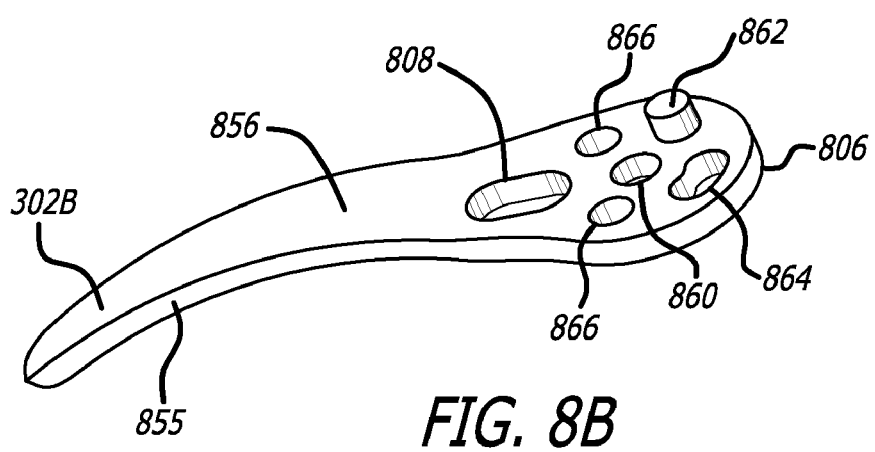
FIG. 8B is a side view of the inner blade of the robotic surgical scissor end effectors.

Refer now to FIGS. 8A-8B, views of a second working element, the inner blade 302B, are illustrated. The inner scissor blade 302B has a drive interface portion 851 and a cutting portion 852 extending there-from. An oval opening 808 extends between the drive interface portion 851 and the cutting portion 852. The oval opening 808, also referred to herein as a crimp receptacle 808, may receive a portion of the crimp 502 of a drive cable 512.

The cutting portion 852 of the blade 302B has a sharpened/honed cutting edge 855 to interface with a sharpened cutting edge 755 of the blade 302A.

The drive interface portion 851 of the blade 302B has a pivot hole or opening 860 and one or more spaced apart drive holes 866, a cam channel 864, and a stop protrusion 862 spaced apart from the pivot hole 860. A lower edge of the drive interface portion 851 may be chamfered and larger in diameter than the drive hubs 306A-306B to form a cable channel 806 for the drive cable 512.

The elements of the drive interface portion 851 of the blade 302B mirror in position the elements of drive interface portion 751 of the blade 302A. Moreover, the functions and features of the pivot hole 860, the drive holes 866, the cam channel 864, the stop protrusion 862, the receptacle 808, and the cable channel 806 are respectively similar to the pivot hole 710, the drive holes 712, the cam channel 714, the stop protrusion 702, the receptacle 708, and the cable channel 706 described previously. The description of the elements of the drive interface portion 751 is incorporated here by reference to describe the elements of the drive interface portion 851 so as to avoid duplication.

Referring now to FIGS. 8A-8B and 9A-9B, the blades 302A-302B may be forged by a variety of stamping methods, include fine blanking and progressive stamping. The blades 302A-302B are forged separately from the drive elements 306A-306B. Forging only the working element as an individual piece may be advantageous because the metal or other material used may be selected based on the properties needed for the working element. For instance Martensitic stainless steel may be selected as the proper material to forge a blade because it can retain a sharp edge. Additionally, Austenitic stainless steel can have the cutting edge of the blade cold worked prior to grinding. This is an extra stamping, forging or coining step applied only to the cutting edge to increase the hardness of the edge, but leaves the rest of the blade ductile so it can resist corrosion. Similarly tungsten carbide may be selected as the proper material to make needle grippers with extreme metal hardness. However due to the brittle nature of tungsten carbide, it may not be the ideal material to form a driving element. Furthermore, hard materials such as tungsten carbide are more difficult to stamp form into complex shapes. The relatively simple shape of the blades 302A-302B or other working element may be manufactured more efficiently as a modular unit. Thus, the independent manufacture of the drive elements and the working elements with the use of different materials may be economically advantageous, even through they require assembly together.

The blades 302A-302B are curved scissors. Initially the blades 302A-302 are stamped flat into straight blades. If flat scissors blades are desired, the post-manufacturing of hardening and sharpening may then occur along the cutting edge of the blade. If curved scissors are desired, the straight blades are bent and formed into curved blades. The bent or curved scissors blades may then be hardened and sharpened along their cutting edge. Curved scissors are usually preferred by surgeons as it allows visibility when cutting tissue under an endoscopic camera of a robotic surgical system.

The material comprising the first working element may be selected to perform in the operative condition of a surgery. Surgical sites are highly saline which may lead to faster corrosion of metals. It is preferable that a choice of metal to operate in a surgical site is highly corrosion resistant. Preferably if the working element performs a shearing or cutting function the metal should also be cable of holding an edge. A metal alloy chosen with these properties may be too brittle to properly function as a drive element. However, because the drive and working elements are modular, no compromise needs to be made when selecting ideal materials. Additional processes, such as cold working or heat treating, are applied to the cutting edge of the blade and are not applied to the drive element which may lead to a cost savings. The drive element material may be a stronger and less brittle metal or perhaps a plastic or composite because it does not need to hold an edge.

Figure 9A:
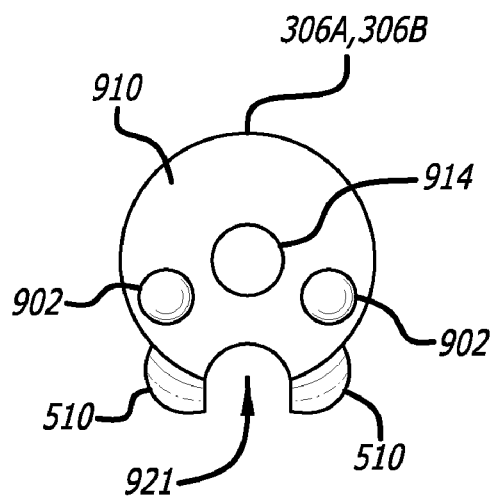
FIG. 9A is a top view of a drive element of the robotic surgical scissor end effectors.
Figure 9C:
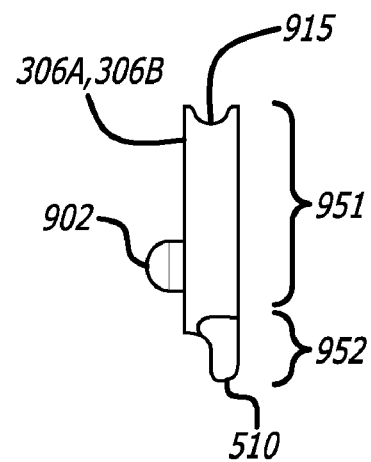
FIG. 9C is a right side view of a drive element of the robotic surgical scissor end effectors.
Figure 9B:
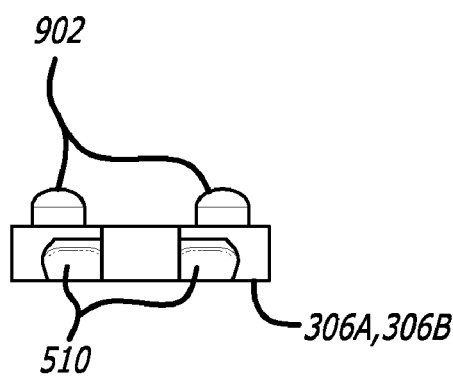
FIG. 9B is a front side view of a drive element of the robotic surgical scissor end effectors.

Referring now to FIGS. 9A-9C, views of the drive elements or drive hubs 306A, 306B are illustrated. When unassembled, the drive elements 306A, 306B are separate pieces from the working elements 302A-302B. As the drive elements and working elements are separate pieces of the end effector, the can be manufactured independently. That is, the drive elements 306A-306B may be formed of a different process with a separate material than that used to make the working elements. As the drive element does not need to hold a sharp edge, such as for a scissor blade, it may be made of a softer metal that is more resistant to stress fractures and other problems sometimes associated with hard brittle metals. The drive element can also be made using a different manufacturing method, such as metal injection molding.

Each of the drive elements or drive hubs 306A-306B may be identical and similarly formed to include a circular drive portion 951 and a retaining portion 952. The drive elements or drive hubs 306A-306B receive the cable 512 and its crimp 502 and removably couple to the working elements.

The retaining portion 952 of each drive element 306A-306B includes a pair of curved protrusions, prongs, or split fingers 510 extending from a top portion of the circular drive portion 951. The curved protrusions, prongs or split fingers 510 have an opening 921 between them to receive the crimp 502 of the cable 512, as illustrated in FIG. 5.

The circular drive portion 951 of each drive element 306A-306B has one or more drive protrusions or drive dogs 902, a pivot hole 914, and the opening 921 extending in from the prongs 510. But for the opening 921, the circular side of the drive portion 951 has a cable groove or channel side 915 as shown in FIG. 9C to receive a portion of the cable 512 to align and guide it around the drive element.

The one or more drive protrusions or drive dogs 902 extending from the circular drive portion 951 of each drive element 306A-306B are received by corresponding drive holes 712, 866 in the respective working elements 302A, 302B. This keys the drive element and the work element of the end effector together.

The pivot hole 914 in the drive interface portion of each drive hub 306A, 306B allows the clevis pin 310 to be inserted through the drive element, providing a pivot point or pivotal axis around which the drive element may pivot or rotate.

Robotic Electrosurgical System and Robotic Electrosurgical Tools

The previous discussion focused on the structure, manufacture, and assembly of two-piece end effectors for robotic surgical tools. The two-piece end effectors may further be used for robotic electro-surgical tools. The two-piece end effectors may be energized as part of a robotic electro-surgical tool. That is the embodiments of the invention, such as the two-piece robotic surgical scissors, may be made hot.

Referring now back to FIG. 1A, a block diagram of a robotic surgery system 100 is illustrated to perform minimally invasive robotic surgical procedures using robotic electro-surgical tools 101A and 101C. Each of the robotic electro-surgical tools 101A and 101C are robotic endoscopic surgical instruments that are manipulated by a slaved robotic manipulator and remotely controlled by control signals received from a master control console. In contrast, manual endoscopic surgical instruments are directly controlled by hand. In one implementation, robotic electro-surgical tool 101A is a bipolar electro-surgical tool. In one implementation, robotic electro-surgical tool 101C is a mono-polar electro-surgical tool.

A user or operator O (generally a surgeon) performs a minimally invasive surgical procedure on patient P by manipulating input devices at a master control console 150. A computer 151 of the console 150 directs movement of robotically controlled endoscopic surgical instruments (generally numbered 101), effecting movement of the instruments using a robotic surgical manipulator 152. The robotic surgical manipulator 152 may also be referred to as robotic patient-side cart system or simply as a cart. The robotic surgical manipulator 152 has one or more robotic arms 153. Typically, the robotic surgical manipulator 152 includes at least three robotic manipulator arms 153 supported by linkages, with a central arm supporting an endoscopic camera and the robotic surgical arms 153 to left and right of center supporting tissue manipulation tools and the robotic surgical tool 101A.

An assistant A may assist in pre-positioning of the robotic surgical manipulator 152 relative to patient P as well as swapping tools or instruments 101 for alternative tool structures, and the like, while viewing the internal surgical site via an assistant's display 154. The image of the internal surgical site shown to A by the assistant's display 154 and operator O by surgeon's console 150 is provided by one of the surgical instruments 101 supported by the robotic surgical manipulator 152.

Generally, the robotic arms 153 of robotic surgical manipulator 152 include a positioning portion and a driven portion. The positioning portion of the robotic surgical manipulator 152 remains in a fixed configuration during surgery while manipulating tissue. The driven portion of the robotic surgical manipulator 152 is actively articulated under the direction of the operator O generating control signals at the surgeon's console 150 during surgery. The actively driven portion of the arms 153 is herein referred to as an actuating portion 158. The positioning portion of the robotic arms 153 that are in a fixed configuration during surgery may be referred to as positioning linkage and/or "set-up joint" 156, 156'.

To support electro-surgical robotic tools 101A, 101B, the robotic surgical system 100 may further include one or more electrosurgical generators 102A-102B. The one or more electrosurgical generators 102A-102B are controlled by the master console 150 over the control cables 109A-109B by a surgeon operating the master console.

The electrosurgical generator 102A is a bipolar generator. A pair of wires 106A-106B couple between the bipolar electrosurgical generator 102A and a bipolar electrosurgical robotic tool 101A. The pair of wires pair of wires 106A-106B may transfer the energy of the bipolar electrosurgical generator 102A to a respective pair of end effectors of the bipolar electrosurgical robotic tool 101A to cauterize or seal tissue.

The electrosurgical generator 102B is a monopolar generator. A wire 107 couples between the monopolar electrosurgical generator 102B and a monopolar electrosurgical robotic tool 101B. A ground wire 108 couples between the monopolar electrosurgical generator 102B and patient P. The wire 107 may transfer the energy of the monopolar electrosurgical generator 102B to an end effector of the monopolar electrosurgical robotic tool 101B to cauterize or seal tissue.

Referring now to FIG. 2A, a perspective view of the robotic surgical manipulator (patient side card) 152 is illustrated. The robotic surgical manipulator 152 has one or more robotic surgical arms 153. The robotic arm 153C includes an electrosurgical robotic tool 101A coupled thereto. The robotic surgical manipulator 152 further includes a base 202 from which the robotic surgical instruments 101 may be supported. More specifically, the robotic surgical instruments 101 are each supported by the positioning linkage 156 and the actuating portion 158 of the arms 153. It should be noted that these linkage structures are here illustrated with protective covers 206, 208 extending over much of the robotic arms. It should be understood that these protective covers 206, 208 are optional, and may be limited in size or entirely eliminated in some embodiments to minimize the inertia that is manipulated by the servomechanism, and to limit the overall weight of robotic surgical manipulator 152.

Each of the robotic surgical tools 101A-101C (collectively referred to by reference number 101) releasably couple to a moveable carriage 237 near an end of each robotic surgical arm. Each moveable carriage 237, with the robotic surgical tool mounted thereto, can be driven to translate along a linear guide formation 260 in the actuating portion 158 of the robotic surgical arms 153 in the direction of arrow 257. The robotic surgical tools 101 are generally sterile structures, often being sterilizable and/or being provided in hermetically sealed packages for use.

Electro Surgical Instruments

Exemplary embodiments of robotic electro surgical tools that can be mounted to a robotic arm in a robotic surgical system are now described. However, further details of robotic electro-surgical tools may be described in U.S. patent Nos. with filing dates and named inventor as follows U.S. Pat. No. 6,840,938, Dec. 21, 2001, Morley et al.; and U.S. Pat. No. 6,994,708, Apr. 18, 2002, Scott Manzo; and application Ser. Nos. 10/726,795, Dec. 2, 2003, Cooper et al.; 10/611,411, Jun. 30, 2003, Manzo et al.; 11/238,698, Sep. 28, 2005, Manzo et al.; and 11/238,794, Sep. 28, 2005, Scott Manzo, all of which are incorporated herein by reference.

Robotic surgical instruments 101 mounted on the robotic surgical arms 153 typically include elongated shafts, with proximal and distal ends. End effectors are generally mounted on wrist-like mechanisms pivotally mounted on the distal ends of the shafts, for enabling the instruments 101 to perform one or more surgical tasks. Generally, the elongate shafts of surgical instruments 101 allow the end effectors to be inserted through entry ports in a patient's body so as to access the internal surgical site. Movement of the end effectors is generally controlled via master controls on the master console 150.

Electrosurgical instruments and systems, as well as methods of performing minimally invasive robotic surgical procedures with such instruments are now disclosed. The instruments of the embodiments of the invention are capable of treating tissue with heat produced by electrical energy while cutting, shearing, grasping, engaging, or contacting treatment tissue. Electrosurgical instruments may apply a high-frequency alternating current to surrounding tissue, thereby to cause the tissue temperature to rise to the point where the tissue is cut or coagulates. Alternatively, electrosurgical instruments may apply heat to tissue by means of electrically generated heat inside the instrument. The electrosurgical treatment may further reduce bleeding of tissue by cauterizing tissue and coagulating blood, or achieve various other desired effects on the treatment tissue such as sealing tissue together. The electrosurgical treatment is carried out in a safe and effective manner that incorporates a variety of safety features to prevent current leakage to non-target tissue so as to reduce collateral tissue damage, unwanted burning, or the like. The fact that a cauterizing action is provided and the nature thereof should not be understood as limiting to the embodiments of the present invention.

Referring to FIGS. 2A-2G, a robotic electro-surgical tool or instrument 400 is illustrated in greater detail than that of instruments 101A and 101C. The robotic electro-surgical tool or instrument 400 includes a mountable housing 401, an elongated shaft 416 having a proximal end and a distal end; and end effectors 414A-414B (collectively referred to by 414) coupled near the distal end of the shaft 416. The mountable housing 401 includes an interface or tool base 412 coupled to the proximal end of the shaft 416. The mountable housing 401 may further include one or more electrical connectors 474, 474A-474B, a cover 472, and one or more release levers 417. At the distal end of the shaft 416 is a mechanical wrist 402 to move the end effectors 414.

The interface or tool base 412 can couple to the adapter 228 to which other surgical tools may also couple so that the electrosurgical tool 400 is removably connectable to the robotic surgical system. During surgery, the adapter 228 is coupled to the moveable carriage 237. Thus, with the electrosurgical tool 400 mounted to the adapter 228, it can translate with the carriage 237 along the actuating portion of the robotic surgical arm 153.

When mounted to a robotic surgical arm 153, end effectors 414 may have a plurality of degrees of freedom of movement relative to arm 153, in addition to actuation movement of the end effectors. As discussed previously, the electrosurgical tool 400 may be translated along an insertion axis as indicated by arrow 257 in FIG. 1B. The elongated shaft 416 is rotatably mounted to the base 412 for rotation about an axis 450 extending longitudinally along the shaft 450 as indicated by the rotational arrow A3. The wrist 402 may be a single pivot wrist, a multi-pivot wrist, a distal roll joint mechanism, or other joints or wrist-like mechanism to provide additional operational degrees of freedom to the end effector. The wrist 402 may pivot around an axis 451 at a pivot point as indicated by the rotational arrow A1. The end effectors 414A, 414B may pivot together as a whole about pivot point 432 as indicated by arrow A2.

The orientation of the mechanical wrist 402 is controlled through pulleys in the tool base 412 and the wrist 402 with cables of cable loops wrapped around each being routed through the shaft 416. The robotic system causes the pulleys in the tool base 412 to be rotated in order to control the position of the mechanical wrist 402, and the end effectors 414. Thus, the cable of the cable loops may also be referred to as a control cable. That is, the end effectors 414 are actuated from the tool base 412 through a cable loop, pulleys, and a spool similar to how other elements of the wrist 402 are controlled. In this case, two cable loops are used to actuate the end effectors 414, one cable loop for each.

Further details of mechanical wrists that may be applicable to the mechanical wrist 402 are described in U.S. patent Nos. with filing dates and named inventor as follows U.S. Pat. No. 5,792,135, May 16, 1997, Madhani et al; U.S. Pat. No. 5,979, 900, May 16, 1997, Madhani et al; U.S. Pat. No. 5,807,377, May 16, 1997, Madhani et al; U.S. Pat. No. 6,206,903, Oct. 8, 1999, Ramans; U.S. Pat. No. 6,312,435, Oct. 8, 1999, Wallace et al.; U.S. Pat. No. 6,371,952, Jun. 28, 1999, Madhani et al; U.S. Pat. No. 6,394,998, Sep. 17, 1999, Wallace et al.; U.S. Pat. No. 6,676,684, Sep. 4, 2001, Morley et al.; U.S. Pat. No. 6,685,698, Jan. 10, 2003, Morley et al.; U.S. Pat. No. 6,699, 235, Mar. 2, 2004, Wallace et al.; U.S. Pat. No. 6,746,443, Jul. 27, 2000, Morley et al.; and U.S. Pat. No. 6,817,974, Jun. 28, 2002, Cooper et al., all of which are incorporated herein by reference.

The end effectors 414 are used in performing a surgical operation such as cutting, shearing, grasping, engaging, or contacting tissue adjacent a surgical site. In one embodiment of the invention, the end effectors 414 includes a pair of gripping jaws for clamping onto tissue. Additionally, a conductor electrically communicates with at least one of the end effectors to deliver electrical energy to tissue clamped by the gripping jaws.

As shown in FIG. 2B, the tool base 412 may be enclosed by a cover 472 which mounts an electrical connector 474. A conductor 448 is electrically coupled to the electrical connector 474 at one end and at least one end effector at the opposite end.

Referring now to FIG. 1D, an insulated conductor 448 passes out from the shaft 416 to the rear of base 412 to the electrical connector 474 for connection to the monopolar electrosurgical generator. The conductor 448 communicates with at least one of the end effectors, to deliver electrical energy to tissue from an electrosurgical generator G, such as the monopolar generator 102B illustrated in FIG. 1A. The tool base 412 may further support a bipolar generator 102A by adding an extra wire connection to the connector 474 or by adding an extra electrical connector 474 and routing two wires to each of the two end effectors.

As discussed previously, the end effectors 414 are actuated from the tool base 412 through a cable of a cable loop, pulleys, and an actuating spool. A cable loop CL may be considered to be a single cable routed in a loop around the drive pulley from the spool in the tool base. A cable loop may be formed by joining or splicing different segments of cable together. Each side of the cable loop CL may be referred to as being a cable. In order to prevent slippage, a cable may be fixed to a pulley, shaft, capstan and/or tube at one point by soldering, welding, crimping or other mechanical fixing means.

The tool base 412 includes actuating spools 434A-434C, guide pulleys 435A-435B, and cable loops CL 436A-436C to form driven elements control the mechanical wrist 402 and the end effectors 414. Each of the driven elements includes receiving elements or input disks (not visible in FIG. 2C, see FIGS. 1D, 2F) that releasably couple through an adapter to a rotatable driving element that is mounted on the carriage 237 of the robotic arm assembly 153. The rotatable driving elements of the carriage 237 are generally coupled to actuators (not shown), such as electric motors or the like, to cause selective angular displacement of each in the carriage 237. Selective actuation of the actuators is transmitted through the rotatable driving element on the carriage 137, to the input disks of the tool 400 and cause selective angular displacement of the actuating spools 434A-434C. This is described in greater detail below with reference to FIGS. 8-12B. Where more or fewer degrees of freedom are desired, the number of spools may be decreased or increased.

Figure 2D:
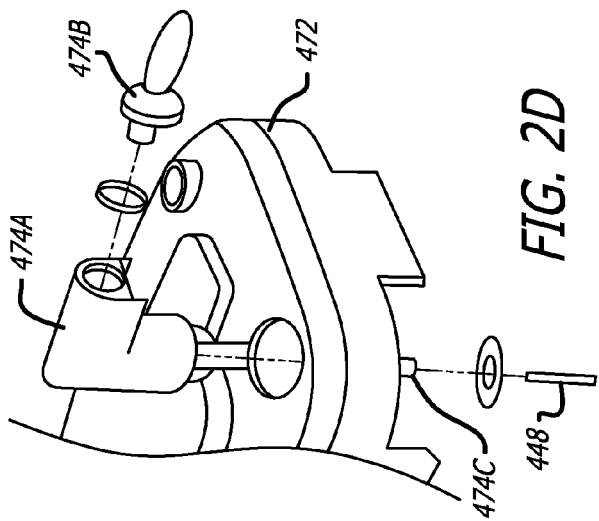
Figure 2E:
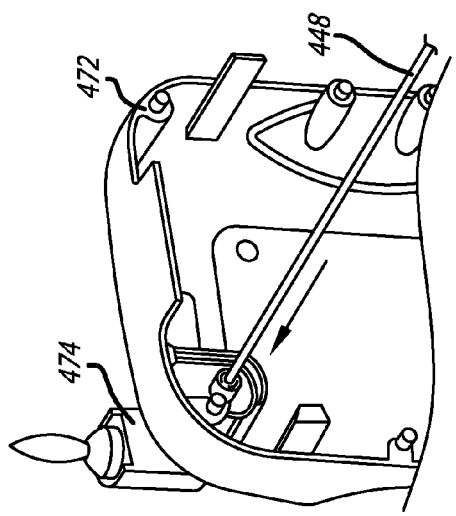
Figure 2C:
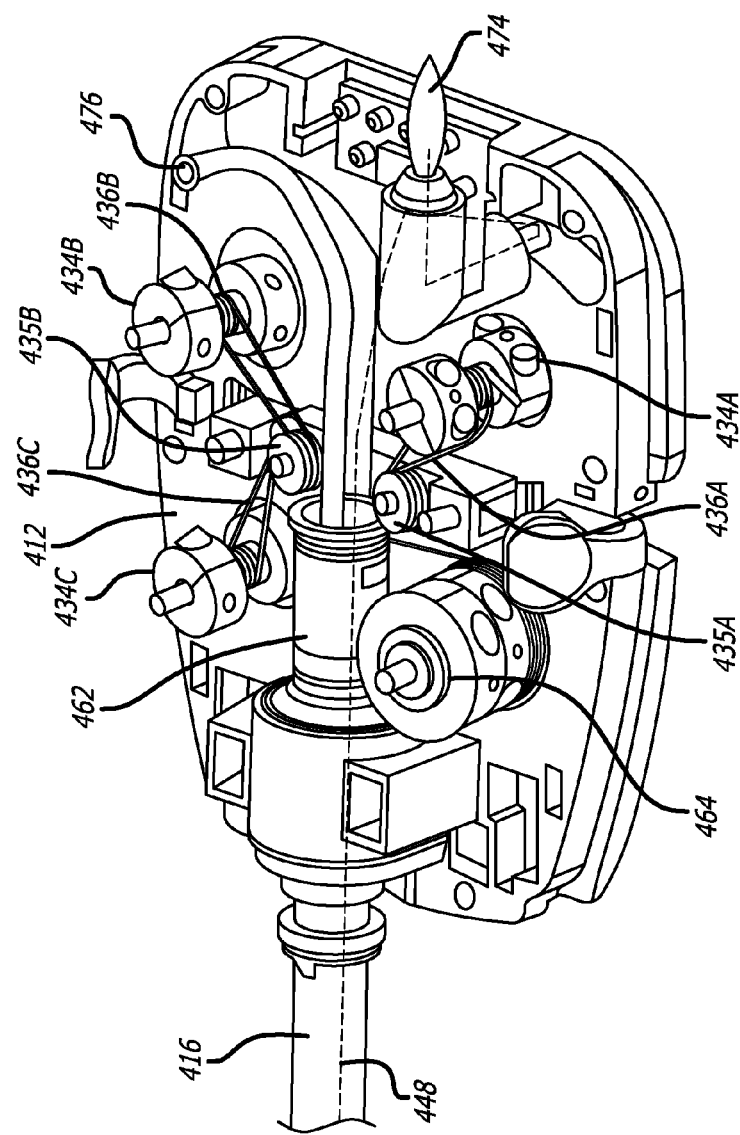
Figure 2F:
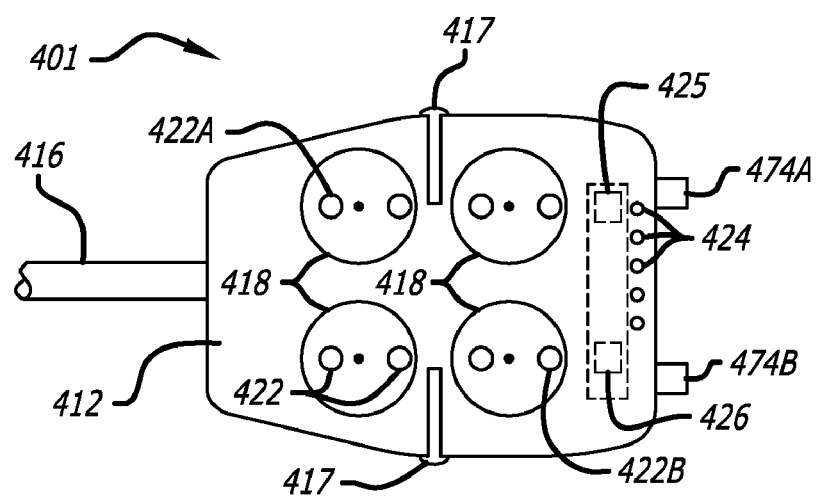
Figure 2G:
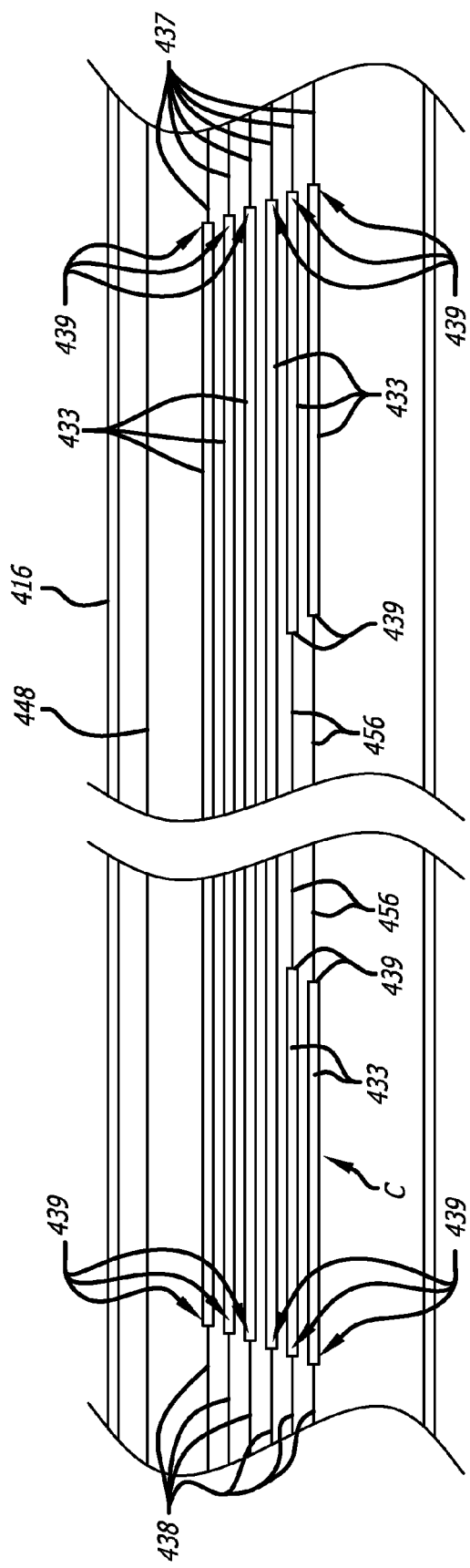

Referring now to FIG. 2G, to inhibit stretching of the cables C along their lengths and along the shaft 416, elongate relatively rigid members, e.g., hypotube portions 33, may be used. The hypotube portions 433 couple to opposed Tungsten cable portions 437, 438 at each end. Ends of the Tungsten cable portions 437, 438 are typically crimped into opposing ends of the hypotubes as indicated by crimps 439. The hypotubes 433 are typically hollow tubes having a circular cross-section. One or more of the cables C may also include a non-conductive portion or an insulator portion 456 coupled between hypotube portions. This may be particularly useful for robotic electro-surgical tools and a live end effector in isolating the current and voltages applied to tissue from other parts of the instrument and system. Regardless of the use of hypotube portions 433 and insulative portions 456, the cabling, hypotube, and insulative portions may be referred to as cables C of a cable loop CL. Note that the cables C, at least in the region of the wrist, are typically made of metal, such as Tungsten or stainless steel, to provide sufficient strength, bendability and durability.

The cables of the cable loops 436A-434C are routed from the actuating spools over the guide pulleys 435A-435B and through the shaft 416 to drive pulleys in the wrist 402. The tool base 412 further includes a spool 464 and a drum 462 with a cable loop coupled there-between to control the rotation of the shaft 416 and the wrist 402.

A first end of the cable of each cable loop is wrapped in one direction around the spool with the second end of the cable wrapped in an opposite direction around the same spool. In this manner, one end of cable is taken up while the other end of the cable is released during the rotation of a spool. Each spool includes a tension mechanism to avoid slack in the cable of each cable loop.

The shaft of each spool extends through the tool base 412 to its underside to couple to an engaging member. The engaging member can releasably couple to a complimentary engaging member that is in turn coupled to an actuator of the surgical system, such as an electric motor, to cause an angular displacement in the spool in response to a control signal from the control console.

An optional flush tube 476 may be mounted to a tool base cover 472 by a flush port 478 and the assembled base 412. The flush tube preferably extends forward (distally) within the base 412 to communicate with the shaft 416 to permit fluids to be passed through the shaft 416 and/or to pressurize the shaft 416. For example, introduction of insufflation gas during surgery or the introduction of cleaning or sterilization gases or fluids prior and/or subsequent to surgery may be passed to the shaft 416 via flush tube 476. U.S. Pat. No. 6,004,509 describes the use of fluids and gases to maintain sterility of a surgical instrument, and is incorporated herein by reference.

Referring now to FIGS. 2D and 2E, the base cover 472 mounts an electrical connector 474, in this case, a banana clip assembly 474a, 474b, and 474c, for the insulated conductor 448 to permit connection to an electrosurgical generator. Note that the connections described above provide an insulated continuous electrical path from the base connector 474 to the end effectors 414A-414B protected from tissue contact except at the jaw portions thereof. Energization of one or both of the end effectors 414A-414B is controllable by the surgeon.

FIG. 2F illustrates a back side view of a portion of the robotic surgical tool 400, some elements of which were previously discussed. In particular, the interface base 412 is illustrated with rotatable receiving elements ("input disks") 418 rotatably coupled thereto. The interface base 412 is used to mount the instrument 400 to a robotic arm of a surgical robotic manipulator. The interface base 412 both mechanically and electrically couples the surgical instrument 400 to a robotic arm of the surgical robotic manipulator 152. The release levers 417 are located at the sides of the mountable housing and may be used to release the robotic surgical instrument 400 from a robotic arm.

The rotatable receiving elements 418 provide a mechanical coupling to the rotatable drivers 234 and drive motors mounted in the robotic surgical arm 153 and the robotic surgical manipulator 152. Each of the rotatable receiving elements 418 includes a pair of pins 422 extending from a surface thereof. An inner pin 422A is closer to an axis of rotation of each rotatable receiving elements 418 than an outer pin 422B, which helps to ensure positive angular alignment of the rotatable receiving elements 418. In one embodiment of the invention, the rotatable receiving elements 418 are disk shaped and are also referred to herein as "input disks".

The interface base 412 further includes an array of electrical connecting pins 424 and one or more integrated circuits 426 coupled to a printed circuit board 425 within the mountable housing 401. As the interface base 412 is backward compatible to the adapter 228, it maybe mechanically actuated by pre-existing driver motors found in the robotic surgical manipulator 152. While the interface base 412 has been described herein with reference to mechanical and electrical coupling elements, it should be understood that other modalities maybe used, including infrared coupling, magnetic coupling, inductive coupling, or the like.

Referring now to FIG. 1D, a schematic view of the electrocautery surgical instrument 400 is illustrated. The electrocautery instrument 400 may be used to generate an electrical current at a surgical site so as to burn or seal, e.g., ruptured blood vessels.

In a monopolar electrosurgical system, the patient is earthed and a voltage is supplied to the electrode coupled to the end effector. An electrically conductive cable 448 extends from a plug 474 on the housing 401 to the electrode at the end effector 812A, 812B. This conductive cable, or cautery wire, may include a "service loop" around a joint axis at the wrist. The service loop, a single loose wrap around the joint, permits rotation of the cautery blade about the axis without placing undue stress or stretch on the wire during such rotation. It will be appreciated that, in use, the plug 474 is releasably connected to an appropriate electrical source. The plug 474 is typically a conventional banana-type plug. The housing 401 is typically of a non-conductive plastics material.

It has been found that it is best to insulate the electrode at the end effectors from the rest of the instrument 400 so as to inhibit current leakage from the electrode to other elements in the instrument 400. It will be appreciated that should the distance between the electrode and the patient be relatively great when a voltage is applied, current may jump from the electrode to other conductive parts of the instrument. In such a case, current can be passed from the instrument 400 to the patient along a path of least resistance, e.g., at the entry port of the shaft coincident with its center of rotation. This may cause unnecessary burning at the entry port. Furthermore, the current may be passed along the instrument 400 to the telesurgical system in general and may be damaging to sensitive electronics, e.g., forming part of the endoscope and viewer arrangement.

Accordingly, the wrist mechanism 402, 850 wherever possible is made of non conductive material. The wrist member 402, 850 and the various pulleys are typically made from non-conductive plastic, e.g., polyethermide or ULTEM. Alternatively, a conductive wrist can be sheathed in a non-conductive material.

The conductive cable 448 is typically sheathed in an insulative material such as, e.g., polytetrafluoroethylene or TEFLON. The conductive cable is electrically coupled the electrode at the end effector 812A, 812B. The electrode may be removably mountable on the end effector 812A, 812B. Accordingly, a conductive seat or sleeve may be used to provide an electrical connection to the electrode when in a mounted condition.

The shaft 416 is typically made entirely from a nonconductive material, or at least sheathed in such a material, to insulate the shaft from the patient, in particular in the region of the port of entry coincident with the center of rotation. One nonconductive material for the shaft comprises an electrical grade fiberglass/vinyl ester composite material. Alternatively, a shaft of stainless steel or carbon fiber may be coated with, e.g., a nylon or parylene, such as Nylon-11 or Parylene C.

The cables that extend internally along the shaft 416 typically have non-conductive portions 456. Such non-conductive or insulative portions are typically high strength polymer cables in the form of, e.g., a liquid crystal polymer (LCP) such as VECTRAN, a liquid crystal polyester. The VECTRAN portions are typically crimped to opposed hypotube lengths. Opposed ends of such hypotubes are in turn typically crimped to tungsten cable lengths which extend to the spools in the housing 401 and to the wrist mechanism 850, respectively.

It will be appreciated that a number of other elements of the tool may also be formed of an insulative material. For example, the pulley arrangement 820, 820B and the wrist member 850 coupled to the distal end of the shaft 416 may be formed of an insulative material such as, e.g., ULTEM.

Electro-Surgical End Effectors

Figure 2H:
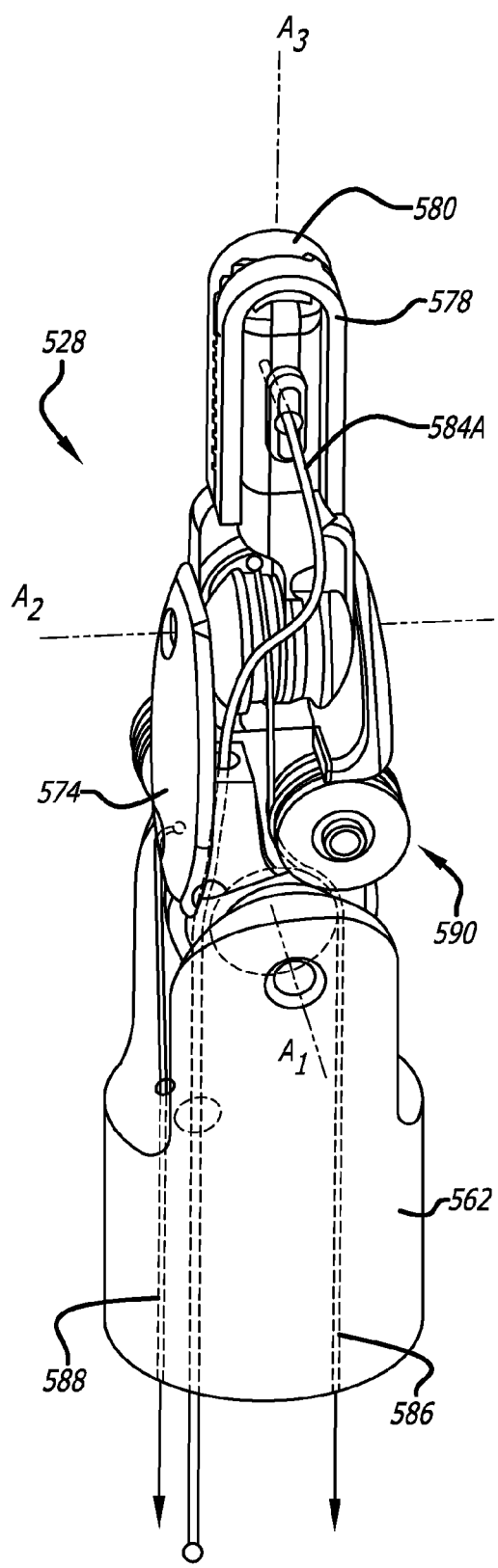
Figure 2I:
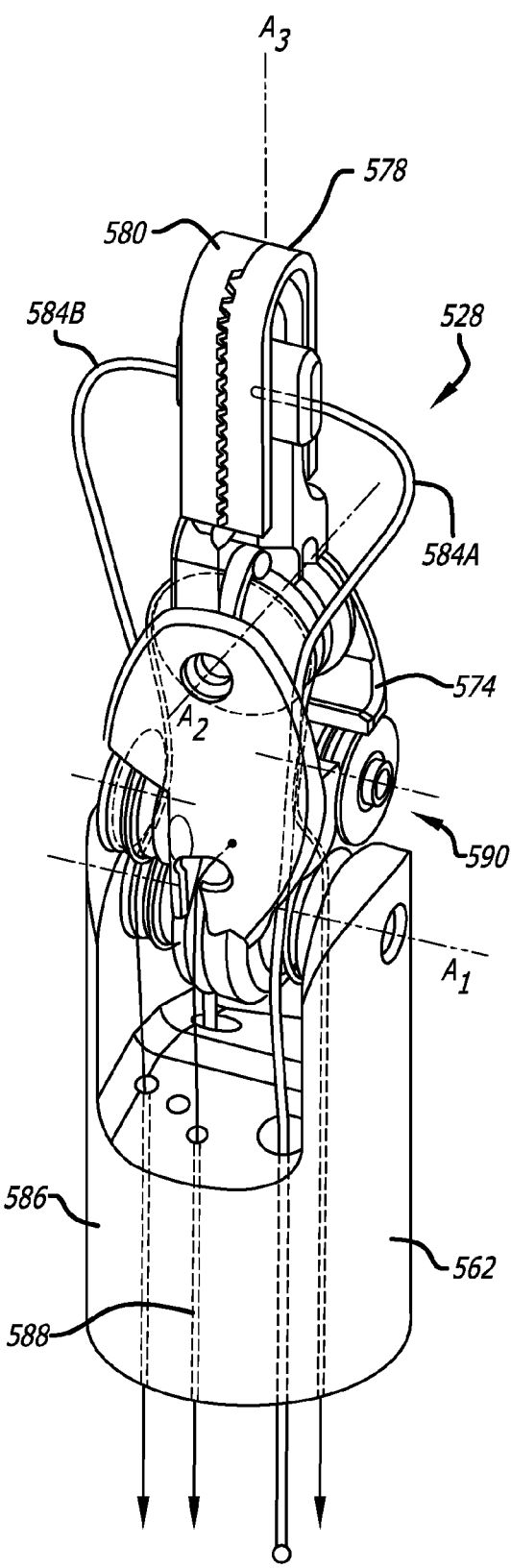

Referring now to FIGS. 2H-2I exemplary cauterizing end effectors are illustrated. U.S. Pat. No. 6,840,938, filed by Morely et al. on Dec. 21, 2001 incorporated here by reference illustrates additional embodiments of cauterizing end effectors or electro-surgical end effectors. In a preferred embodiment of the invention, the cauterizing end effectors or electro-surgical end effectors are each of a two-piece design including a drive element and a working element as previously described herein with reference to FIGS. 3-9C.

FIGS. 5A-5B, illustrate a portion of an exemplary bipolar cauterizing tool 528. A wrist 574 is rotatably coupled to shaft 562 about the first axis A1. End effectors 578, 580 are rotatably coupled to the wrist 574 about a second axis A2. Both the end effectors and the wrist can rotate together about the longitudinal axis A3 of the shaft 562. A negative and positive electrode 582A, 582B (shown most clearly in FIGS. 6A and 6B) can be coupled to the end effectors to deliver a high frequency electrical energy into tissue engaged by the jaws 578, 580.

The conductive electrodes 582A, 582B can be coupled to an electric power supply (see the bipolar generator 102A illustrated in FIG. 1A) through conductive leads 584A, 584B. In an exemplary embodiment, the conductive leads can be run from the tool base end of the instrument, through the shaft 562, through lumens in wrist 574, and up to the electrodes 582A, 582B disposed on the end effectors 578, 580. The distal portion of the conductive leads 584A, 584B can be run outside of the wrist 574 so as to allow for easy connection and disconnection of the conductive leads 584A, 584B from the electrodes.

Depending on the specific configuration of the cauterizer, the end effectors 578, 580 and drive system can be composed of a nonconductive material or a conductive material. In some embodiments, the electrodes can be insulated from the end effector with either a nonconductive bushing or sleeve that is composed of plastic, ceramic, TEFLON, ULTLEM, or other non-conductive materials. If the electrodes are attached directly to the end effectors, an insulating bushing can be disposed between the conductive end effectors and the electrodes so that the only "live" portion of the surgical instrument are the electrodes.

The electrodes of the present invention are preferably made of a conductive material such as aluminum, stainless steel, platinum, tungsten, gold, or the like. The electrodes can be in the form of strips, deposited material, inserts, or the like. In some embodiments, the jaws themselves can be the electrodes.

For the bipolar methods of the present invention, the two electrodes on the end effectors should be at two electrical potentials and should not come in contact with each other. Thus, in most embodiments the electrodes are configured to have a gap between the electrodes even when the end effectors are in a closed configuration. As is the case with conventional electrosurgical instruments, a range of supply settings may be used for cutting, coagulation and the like. Moreover, it should be appreciated, that the electrodes can be configured in a wide variety of patterns and designs.

An exemplary power supply can create a wattage up to approximately one-hundred-twenty (120) Watts of power for cauterizing the target tissue. The voltage used with a bipolar robotic cauterizer tool is generally between zero (0) volts (V) and one thousand (1000) V peak-to peak, and preferably between one-hundred (100) V and five-hundred (500) V. As long as the jaws and electrodes are both in good contact with the tissue intended to be cauterized and/or cut, there is much less chance of voltage from the electrodes arcing to other conductive components on the instrument (e.g., the wrist, shaft, or pulleys). It should be appreciated, however, that the voltage setting of the electrosurgical power generator will vary depending on the specific dimensions of the electrodes, the tissue to be treated, and the like.

In exemplary embodiments, movement of end effectors 578, 580 are effected through mechanical actuation of a yaw cable 586 and pitch cable 588 via surgeon input devices. Actuation of the pitch cable 588 can rotate the end effectors 578, 580 about the wrist axis A1, while actuation of the yaw cable 586 moves the jaws about axis A2, an axis that is substantially perpendicular to axis A1, between an open and closed position. Typically, the cables 586, 588 are directed through lumens in the shaft and wrist body and through a conductive or nonconductive pulley assembly 590.

It should be appreciated that the electrodes can be positioned on opposing end effector or on the same end effector. Moreover, the electrodes do not have to be disposed within a groove or on a boss. The electrodes can contact the engaged tissue disposed between the electrodes 582A, 582B and a current is applied between the spaced electrodes to deliver a current flow to cauterize the tissue. If desired, a tension force applied from the end effectors can cut the tissue along the cauterization heat lines to separate the tissue. In this case, the jaws can optionally include a cutting blade disposed on the jaws to facilitate cutting of the tissue. The blade can be stationary or spring loaded and may be conductive or nonconductive.

Drive System

Referring now to FIG. 1C, a simplified illustration of a drive system is shown to mechanically couple servomotors 802A to the end effectors 812A, 812B, respectively through a set of cables and pulleys. The end effectors 812A, 812B may be two piece end effectors as described here, such as the tow piece end effectors 601A-601B illustrated in FIG. 6 for example. The drive system further mechanically couples another servomotor to move a joint of the wrist 850 of the robotic surgical tool through another set of cables and pulleys. The drive system further still mechanically couples another servomotor to the shaft 416 of the robotic surgical tool through still another set of cables and pulleys.

The drive system includes a tool drive portion 800A and a robotic surgical arm portion 800B that are coupled together at an interface 810. The tool drive portion 800A corresponds to the drive system in the robotic surgical tool 400. The robotic surgical arm portion 800B corresponds to the drive system in the robotic surgical arm 153.

The tool drive portion 800A of the drive system 800 receives mechanical inputs from the robotic surgical arm portion 800B through driven elements 818A-818D, including input disks. From the driven element 818C, the tool drive portion of the drive system translates mechanical inputs from driven element 818C into articulation of a wrist member 850 about the first axis A1. From the driven elements 818A-818B, the tool drive portion of the drive system translates mechanical inputs from the driven element 818A-818B into articulation of the wrist 850 about the first axis A2 as well as into actuation of the two element end effectors 812A, 812B by relative movement of the end effector elements about axis A2. From the driven element 818D, the tool drive portion of the drive system translates mechanical inputs from driven element 818D to effect rotation of the end effectors 812A-812B and the wrist 850 about the axis A3 of shaft 416 by rotating the shaft relative to housing 401 over a limited angle of rotation. In FIG. 8, the rotational motion of shaft 416 about axis A3 is omitted in order to more easily show other elements of the system. Care should be taken to prevent over-rotation of the shaft that may cause cables therein to twist into contact with each other and create friction between the cables.

The robotic surgical arm portion 800B of the drive system 800 includes servomotors 802A-802D that are mechanically coupled to rotatable driver pulleys 828A-828D through cable loops CL5-CL8 to transfer rotation of the servomotors to the rotatable driver pulleys. The servomotors 802A-802D may be standard drive motors having position encoders. However, other actuators may be used, such as hydraulic actuators and piezoelectric motors. To be used as an actuator in the present surgical instrument a drive mechanism should be able to provide variable and controllable force and position control. Capstans 804A-804D are coupled to shafts of the respective servomotors 802A-802D. A pair of ends of each cable loop CL5-CL8 are wrapped within a spiral groove around the capstans 804A-804D so that one end is payed out as one end is take in. A pair of opposite ends of the cable loops CL5-CL8 are wrapped around opposite sides of a pulley of the rotatable driver pulleys 828A-828D. The cable loops CL5-CL8 may also move over one or more idler pulleys 830-840 between the capstans 828A-828D and the rotatable driver pulleys 828A-828D. Additionally, the robotic surgical tool 400 moves along a carriage 237 such that the cable loops CL5-CL8 and one or more idler pulleys 830-840 may adjust in position to allow for the movement in the robotic surgical tool which is not shown in the simplified FIG. 1C.

At the interface 810, the rotatable driver pulleys 828A-828D of the robotic surgical arm portion couple to the driven elements 818A-818D of the tool drive portion 800A when the robotic surgical tool 400 is mounted to the robotic surgical arm. The driven elements 818A-818D couple to the rotatable driver pulleys 828A-828D respectively through an adapter that is not shown in the simplified FIG. 8.

When the rotatable driver pulleys 828A-828D of the robotic surgical arm portion couple to the driven elements 818A-818D of the tool drive portion 800A, the servo motor 802A can drive the driven pulley 820A and the end effector 812A. The servo motor 802B can drive the driven pulley 820B and the end effector 812B. The servo motor 802C can drive the driven pulley 882 and yaw the wrist 850. The servo motor 802D can drive the drum 884 and rotate the shaft to roll the wrist 850.

Referring back to the tool portion 800A of the drive system, end effectors 812A, 812B; wrist member 850, and the shaft 416 of the tool 400 are driven by cable loops CL1, CL2, CL3, and CL4 arranged into an actuation scheme around a plurality of pulleys. The actuation scheme allows the actuation of a three degree-of-freedom wrist using four cable loops. Alternative actuation schemes using more or less cable loops and cables may be desirable in situations where the forces required for actuation of different motions differ greatly in magnitude. Employing cables instead of gears to control the robotic surgical tool 400 minimizes the amount of friction and backlash within instrument. The combination of small moving masses and low friction enables instrument 400 to provide force reflection to the master control computer 151 at the master console 150 with high sensitivity.

Cable loop CL1 drives end effector 812A and includes a first cable CIA and a second cable C1B forming two sides of the cable loop. The first cable CIA engages the driven element 818A at one end in a first direction, wraps over one or more intermediate idler pulleys 870 in the wrist 850, and couples to the driven pulley 820A at a second end in a first direction. The second cable C2A engages the driven element 818A at one end in a second direction, wraps over one or more intermediate idler pulleys 876 in the wrist 850, and couples to the driven pulley 820A at a second end in a second direction.

Cable loop CL2 drives end effector 812B and includes a first cable C2A and a second cable C2B forming two sides of the cable loop. The first cable C2A engages the driven element 818B at one end in a first direction, wraps over one or more intermediate idler pulleys 872 in the wrist 850, and couples to the driven pulley 820B at a second end in a first direction. The second cable C2A engages the driven element 818B at one end in a second direction, wraps over one or more intermediate idler pulleys 874 in the wrist 850, and couples to the driven pulley 820B at a second end in a second direction.

Cable loop CL3 drives a pulley 882 in the wrist 850 to rotate it about axis A1 and includes a first cable C3A and a second cable C3B forming two sides of the cable loop. The first cable C3A engages the driven element 818C at one end in a first direction and couples to the driven pulley 882 at a second end in a first direction. The second cable C3B engages the driven element 818C at one end in a second direction and couples to the driven pulley 882 at a second end in a second direction.

Cable loop CL4 drives a drum 884 in the housing 401 that is coupled to the shaft 416 to rotate it about axis A3. Similar to the cable loop CL3, the cable loop CL4 and includes a first cable and a second cable forming two sides of the cable loop that are coupled on opposite sides to each of the drum 884 and the driven element 818D.

Referring now to FIG. 1D, further details of the drive system 800 for an end effector 812A is illustrated with respect to the robotic surgical tool 400 and the robotic surgical arm 153. A second end effector may be similarly controlled by duplicate elements.

In FIG. 1D, servomotor 802A is mechanically coupled by the drive system 800 to the end effector 812A through a series of cables and pulleys.

Cables C5A-C5B of the cable loop CL5 mechanically couple the servomotor 802A to the rotatable driver pulley 828A in the robotic surgical arm 153. The capstan 804A is coupled to the drive shaft 904A of the servomotor 802A. A pair of ends of the cable loop CL5 are wrapped within a spiral groove around the capstan 804A so that one end of the cable C5A is payed out as one end of cable C5B is taken in and visa-versa. The pair of ends at the opposite end of the cable loop CL5 are wrapped around opposite sides of the pulley 928A of the rotatable driver pulley 828A to match the linear direction of the cables C5A-C5B, as one is taken up the other is payed out. The cable loop CL5 may also move over one or more idler pulleys 831-832 between the capstan 804A and the pulley 928A of the rotatable driver pulley 828A. Through the cable loop CL5, capstan 804A, and pulley 928A, the rotation of the servomotor 802A is mechanically coupled to the rotatable driver pulley 828A.

The rotatable driver pulley 828A mechanically couples to the input disk 918A of the driven element 818A by means of a rotatable adapter 910A at the interface 810.

In the robotic surgical tool 400, cables C1A-C1B of the cable loop CL1 mechanically couple the driven element 818A to the driver pulley 820A and its end effector 812A. One end of each of the cables C1A-C1B of the cable loop CL1 wrap around and couple to the actuating spool 920A of the driven element 818A. The opposite end of each of the cables C1A-C1B of the cable loop CL1 wrap around opposite sides and couple to the driven pulley 820A. The cable loop CL1 may also move over one or more idler pulleys 870 between the input disk 918A and the pulley 820A. Through the cable loop CL1, input disk 918A, and pulley 820A, the rotation of the driven element 818A is mechanically coupled to the pulley 820A and the end effector 812A.

Generally, rotation of the elements 818A-818D in a first direction causes the pulleys to rotate in a first direction by pulling on a first side of the cable loop and paying out the second side of the cable loop. Rotation of the elements 818A-818D in a second direction causes the pulleys to rotate in a second direction by pulling on the second side of the cable loop and paying out the first side of the cable loop.

In the tool portion 800A, the amount of rotation of the driven elements 818A-818D that is transferred into rotation at the axes A1-A3 is a function of the radius of the actuating spools (such as spool 920A) at the driven elements, about which the cables wrap at one end, and the radius of the driven pulleys 820A, 820B, 882 and drum 884 at the second end. Actuating spools can be chosen with differing radius at the driven elements 818A-818C to obtain more or less rotation in the driven members given that the driven pulleys 820A, 820B, 882 are often constrained by size limitations at the distal end of the shaft 416 of the robotic surgical tool. However, with larger shaft diameters the radius of the driven pulleys 820A, 820B, 882 can be increased to provide a greater range of motion and force. Additionally, the radius of the driven pulleys 820A, 820B, 882 may be chosen to allow the cables to properly engage idler pulleys. For example, driven pulleys 820A-820B may have different diameters in order to allow their cables to suitably engage their respective intermediate idler pulleys. Additionally, the radius of idler pulleys may be chosen to keep the cables they are guiding straight but are preferably small to minimize space requirements.

At the interface 810, the ratio of the radius of rotatable driver pulleys 828A-828D to the radius of the actuating spool of the driven elements 818A-818D acts like a transmission. The ratio of these radiuses change the amount of linear distance of cable that is pulled in and payed out at the actuating spool in the robotic surgical tool from that of the linear distance of cable that is pulled in and payed out at the rotatable driver pulleys 828A-828D.

In the robotic surgical arm portion 800B, the amount of rotation of the capstans 818A-818D at the motors 802A-802D that is transferred to the rotatable driver pulleys 828A-828D is a function of the radius of the capstans 818A-818D and the radius of the rotatable driver pulleys 828A-828D. As these elements are found in the robotic surgical arm, their radius are constant for each type of tool that is mounted to the robotic surgical arm.

For the servomotors 802A-802B to drive the end effectors 812A-812B, a torque differential coupling matrix may be used to provide a translation of torque at the servomotors to the driven pulleys 802A-820B about their respective axis. For the servomotors 802C-802D to respectively drive the driver pulley 882 and the drum 882, the coupling matrix is also used to translate a torque at the servomotors to the driven pulley 882 and drum 884 about their respective axis. At the end effectors 812A-812B, the torque at the driven pulleys 802A-802B can be simply converted into a linear force at tips of the end effectors knowing the radius of the pulleys and the length of the end effectors extending beyond the pulleys. This linear force at the tips of the end effectors is often referred to as a tip force.

CONCLUSION

While certain exemplary implementations have been described and shown in the accompanying drawings, it is to be understood that such implementations are merely illustrative of and not restrictive to the specific constructions and arrangements shown and described. For example, implementations were particularly described with reference to robotic surgical scissor end effectors. However, other implementations of the invention may be to different types of end effectors. As another example, two drive hubs 306A-306B for end effectors have been shown and described herein in detail. However, some embodiments of the invention may only employ a single drive hub that may be used interchangeably with one or more working elements. For example, a single drive hub design may be compatible with both straight and curved scissors, or with both a scissors tool and a gripping tool. With this in mind, the embodiments of the invention should be construed according to the claims that follow below.

What is claimed is:

1. An apparatus for robotic surgery, the apparatus comprising:
   a first metal scissor blade having a first drive interface portion, a first cutting portion extending from the first drive interface portion, and a first oval opening extending between the first drive interface and the first cutting portion to receive a first metal crimp of a first cable, wherein
      the first drive interface portion having a first pivot hole, a first pair of drive holes spaced from the first pivot hole, a first cam channel having a pair of end stops spaced from the first pivot hole, and a first stop protrusion spaced from the first pivot hole, wherein the first pair of drive holes to receive a first pair of drive dogs, the first cam channel to receive a second stop protrusion, the first stop protrusion to be inserted into a second cam channel,
      and
      the first cutting portion having a first cutting edge;
   and,
   a second metal scissor blade having a second drive interface portion, a second cutting portion extending from the second drive interface portion, and a second oval opening extending between the second drive interface portion and the second cutting portion to receive a second metal crimp of a second cable, a surface of the second drive interface to rotatingly mate with a surface of the first drive interface, wherein
      the second drive interface portion having a second pivot hole to align with the first pivot hole, a second pair of drive holes radially spaced from the second pivot hole, the second cam channel having a pair of end stops radially spaced from the second pivot hole, and the second stop protrusion radially spaced from the second pivot hole, wherein the second pair of drive holes to receive a second pair of drive dogs, the second cam channel to receive the first stop protrusion, the second stop protrusion to be inserted into the first cam channel,
      and
      the second cutting portion having a second cutting edge.

2. The apparatus of claim 1, wherein
the first metal scissor blade and the second metal scissor blade are each stamped from a metal blank.

3. The apparatus of claim 1, further comprising:
   a first drive hub having a first circular drive portion and a first pair of curved protrusions extending from a top surface of the first circular drive portion, wherein
      the first circular drive portion having a third pivot hole to align with the first and second pivot holes, the first drive dogs extend from a surface of the first circular drive portion to be inserted into the first drive holes to drive the first metal scissor blade, and a first cable groove side to receive the first cable, and
      the first pair of curved protrusions to capture the first metal crimp of the first cable between them and the first oval opening;
   and,
   a second drive hub having a second circular drive portion and a second pair of curved protrusions extending from a top surface of the second circular drive portion, wherein the second circular drive portion having a fourth pivot hole to align with the first, second, and third pivot holes, the second drive dogs extend from a surface of the second circular drive portion to be inserted into the second drive holes to drive the second metal scissor blade, and a second cable groove side to receive the second cable, and the second pair of curved protrusions to capture the second metal crimp of the second cable between them and the second oval opening.

4. The apparatus of claim 3, wherein the first metal scissor blade and the second metal scissor blade are each formed using a first metal material, and the first drive hub and the second drive hub are each formed using a second metal material differing from the first metal material.

5. The apparatus of claim 1, wherein the first metal material has a first material strength, the second metal material has a second material strength, and the second metal material differs from the first metal material because the second material strength of the second metal material is greater than the first material strength of the first metal material.

6. The apparatus of claim 1, further comprising:

a first washer having a fifth pivot hole;

a second washer having a sixth pivot hole;

a clevis housing coupled to a wristed joint at a first end and having a c-shaped opening at a second end opposite to the first end to receive the first washer, the first drive hub, the first drive interface portion, the second drive interface portion, the second drive hub, and the second washer, the clevis housing further having a top pin opening and a bottom pin opening aligned together and perpendicular to the c-shaped opening; and a pivot pin having a first end to couple to the bottom of the clevis housing and a second end to couple to the top of the clevis housing, the pivot pin to be inserted through the top pin opening, the fifth pivot hole, the first pivot hole, the second pivot hole, the third pivot hole, the fourth pivot hole, the sixth pivot hole and the bottom pin opening to pivotally couple together the first washer, the first drive hub, the first metal scissor blade, the second metal scissor blade, the second drive hub, and the second washer; and wherein the wristed joint is coupled to a shaft of a robotic surgical tool.

* * * * *